United States Patent [19]

Janda

[11] Patent Number: 5,187,086
[45] Date of Patent: Feb. 16, 1993

[54] MOLECULES WITH ANTIBODY COMBINING SITES THAT CATALYZE HYDROLYSIS REACTIONS THROUGH USE OF A CHARGED HAPTEN

[75] Inventor: Kim Janda, San Diego, Calif.

[73] Assignee: Scripps Clinic and Research Foundation, La Jolla, Calif.

[21] Appl. No.: 644,909

[22] Filed: Jan. 23, 1991

Related U.S. Application Data

[63] Continuation-in-part of Ser. No. 470,924, Jan. 26, 1990, abandoned.

[51] Int. Cl.$^5$ .............................. C12P 7/42; C12N 9/00
[52] U.S. Cl. .................................. 435/146; 435/188.5; 435/183; 435/197; 435/240.26
[58] Field of Search ............... 435/183, 197, 212, 219, 435/188.5, 240.26, 146; 530/387, 388, 387.1, 388.1

[56] References Cited

U.S. PATENT DOCUMENTS 4,792,446 12/1988 Kim et al. ..................... 424/94.1

FOREIGN PATENT DOCUMENTS 8502414 6/1985 PCT Int'l Appl. .

OTHER PUBLICATIONS

Lerner, R. A., et al, (1988) Bioassays 9, 102–112.
Shokat, K. M., et al, (1989) Nature 338, 269–271.
Janda, K. D., et al, (1990) J. Am. Chem. Soc., 112, 1274–1275.
Janda, K. D., et al, (1990) Biotechnol Prog. 6, 178–181.
Slobin, Biochemistry, 5(9):2836–2844 (1966).
Kohen et al., FEBS Letters, 100(1):137–140 (1979).
Kohen et al., Biochim. Biophys. Acta, 629:328–337 (1980).
Kohen et al., FEBS Letters, 111:427–431 (1980).
Jencks, Adv. Enzymol., 43:219–221, 312–317 (1975).
Jencks, Catalysis in Chemistry and Enzymology, pp. 287–289, (McGraw-Hill, N.Y. (1969).
Tramontano et al., Science, 234:1566–1570 (1986).
Pollack et al., Science, 234:1570–1573 (1986).
Jacobs et al., J. Am. Chem. Soc., 109:2174–2176 (1987).
Tramontano et al., Proc. Natl. Acad. Sci., USA, 83:6736 (1986).
Napper et al., Science, 237:1041 (1987).
Janda et al., Am. Chem. Soc., 110:4835 (1988).
Janda et al., Science, 241:1188 (1988).
Janda et al., Science, 244:437 (1989).
Pollack et al., Science, 242:1038 (1988).
Pollack et al., J. Am. Chem. Soc., 111:1929 (1989).
Baldwin et al., Science, 245:1104 (1989).
Pressman et al., J. Am. Chem. Soc., 68:250 (1946).
Pressman et al., J. Am. Chem. Soc., 75:686 (1953).
Grossberg et al., J. Am. Chem. Soc., 82:5470 (1960).
Sastry et al., Proc. Natl. Acad. Sci. USA, 86:5728 (1989).
Huse et al., Science, 246:1275 (1989).

Primary Examiner—Charles L. Patterson, Jr.
Attorney, Agent, or Firm—Dressler, Goldsmith, Shore, Sutker & Milnamow, Ltd.

[57] ABSTRACT

An antibody molecule or molecule containing antibody combining site portions (catalytic molecule) that catalytically hydrolyzes a preselected carboxylic acid amide or ester bond of a reactant ligand, methods of making and using the catalytic molecule, and cells that produce those molecules are disclosed. The catalytic molecules bind to a reactant ligand containing the bond to be hydrolyzed and also to a haptenic ligand. The haptenic ligand is structurally analogous to the reactant ligand and contains a tetrahedral carbon atom that is bonded to a hydroxyl group and to a saturated carbon atom at a position in the haptenic ligand that corresponds to position of the carbonyl group and its bonded heteroatom of the reactant ligand. The haptenic ligand also contains a group that bears an ionic charge in aqueous solution at physiological pH values that is not present at a corresponding position of the reactant ligand. The ionic charge-bearing group is located in the hapten within 7 Ångstroms of the tetrahedral carbon atom.

16 Claims, 4 Drawing Sheets

FIGURE 1
FIG. 1A
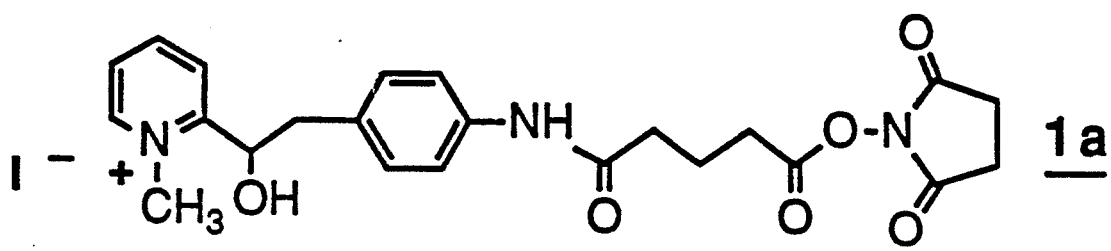
1a
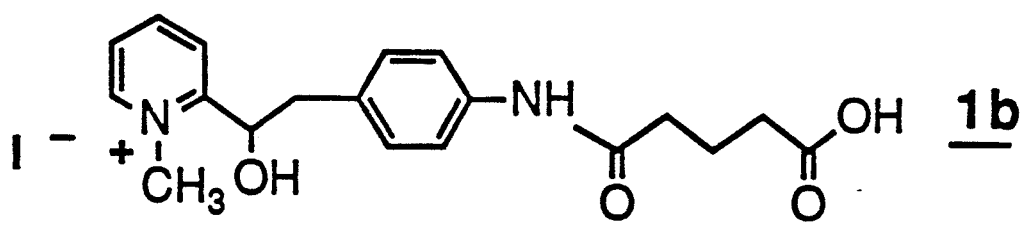
1b
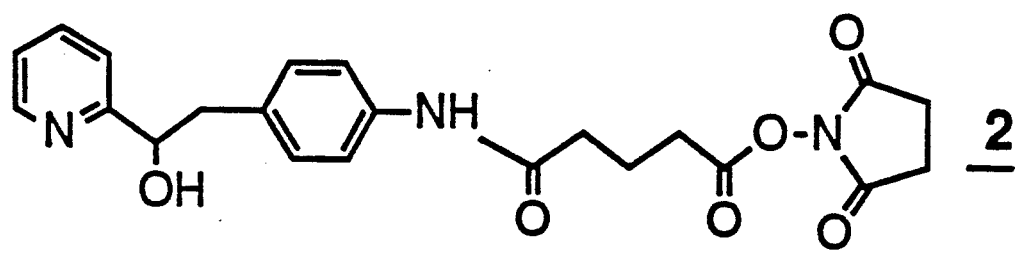
2
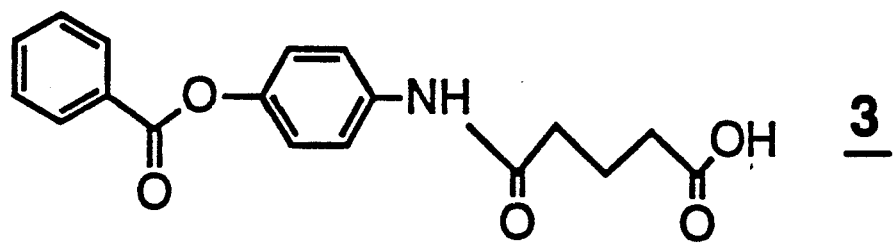
3

4

5a

6

7

FIGURE 2
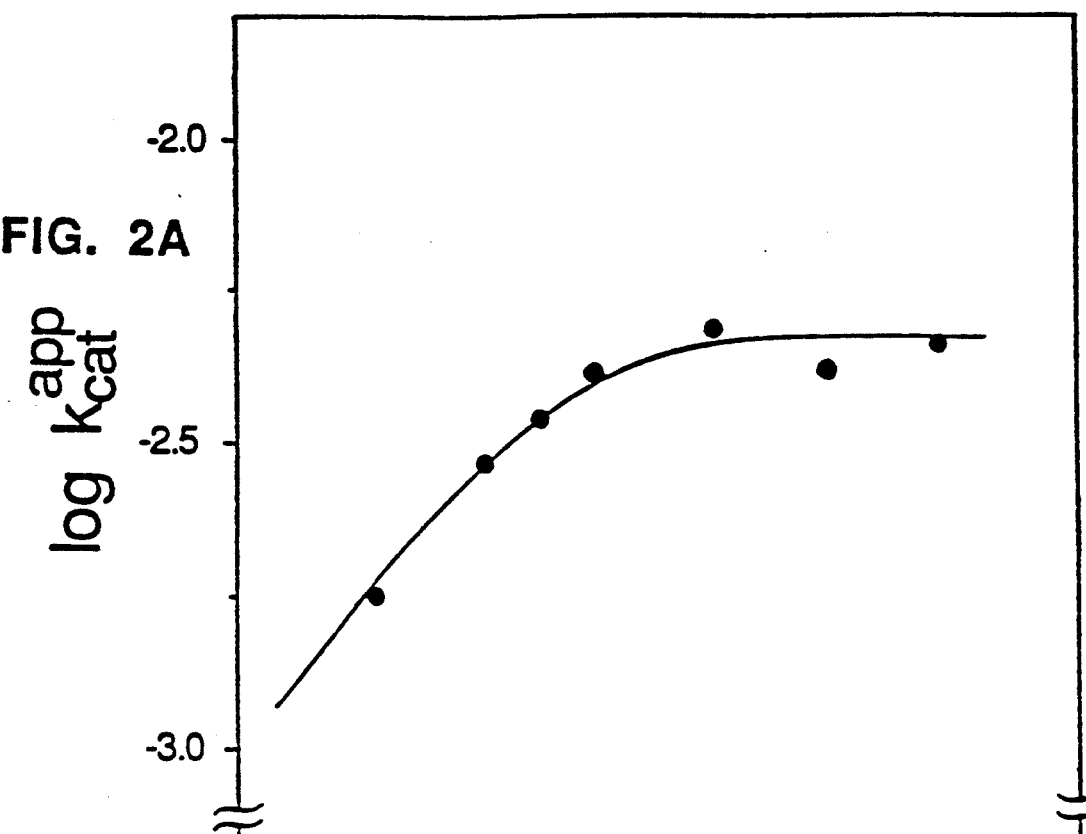
FIG. 2A
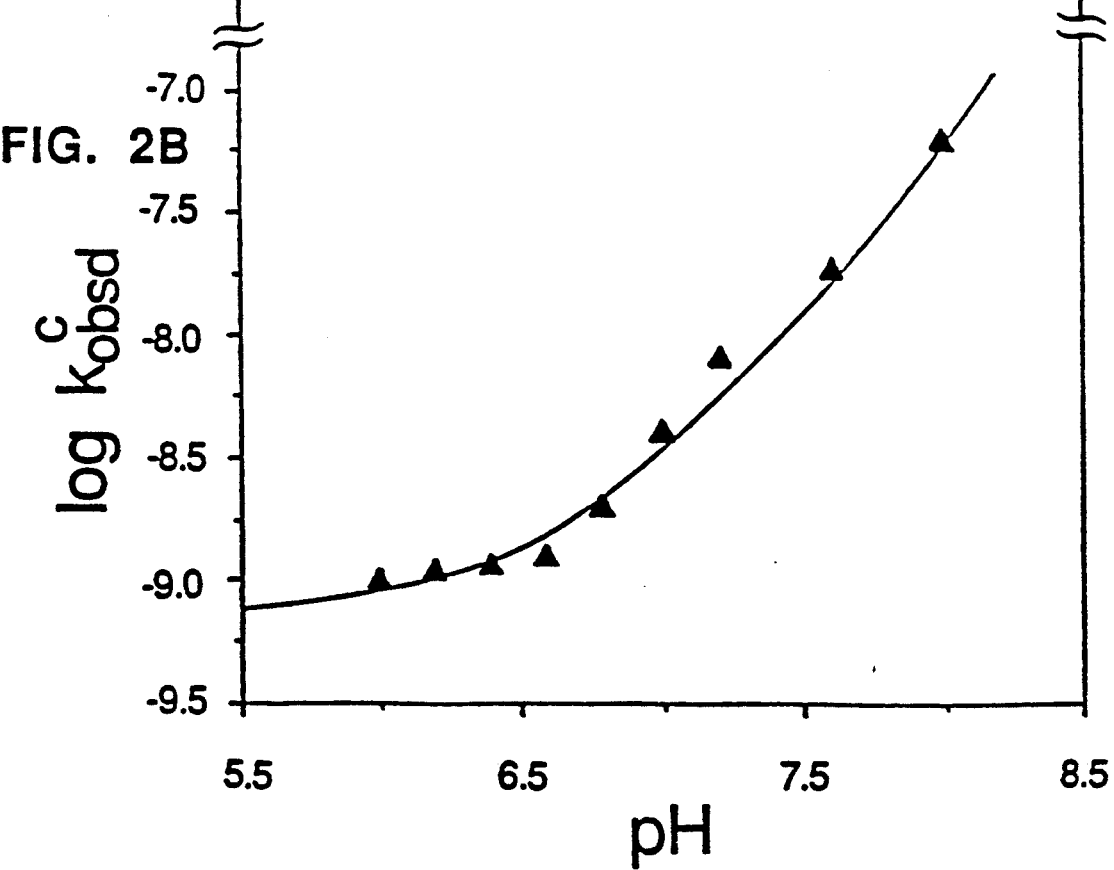
FIG. 2B

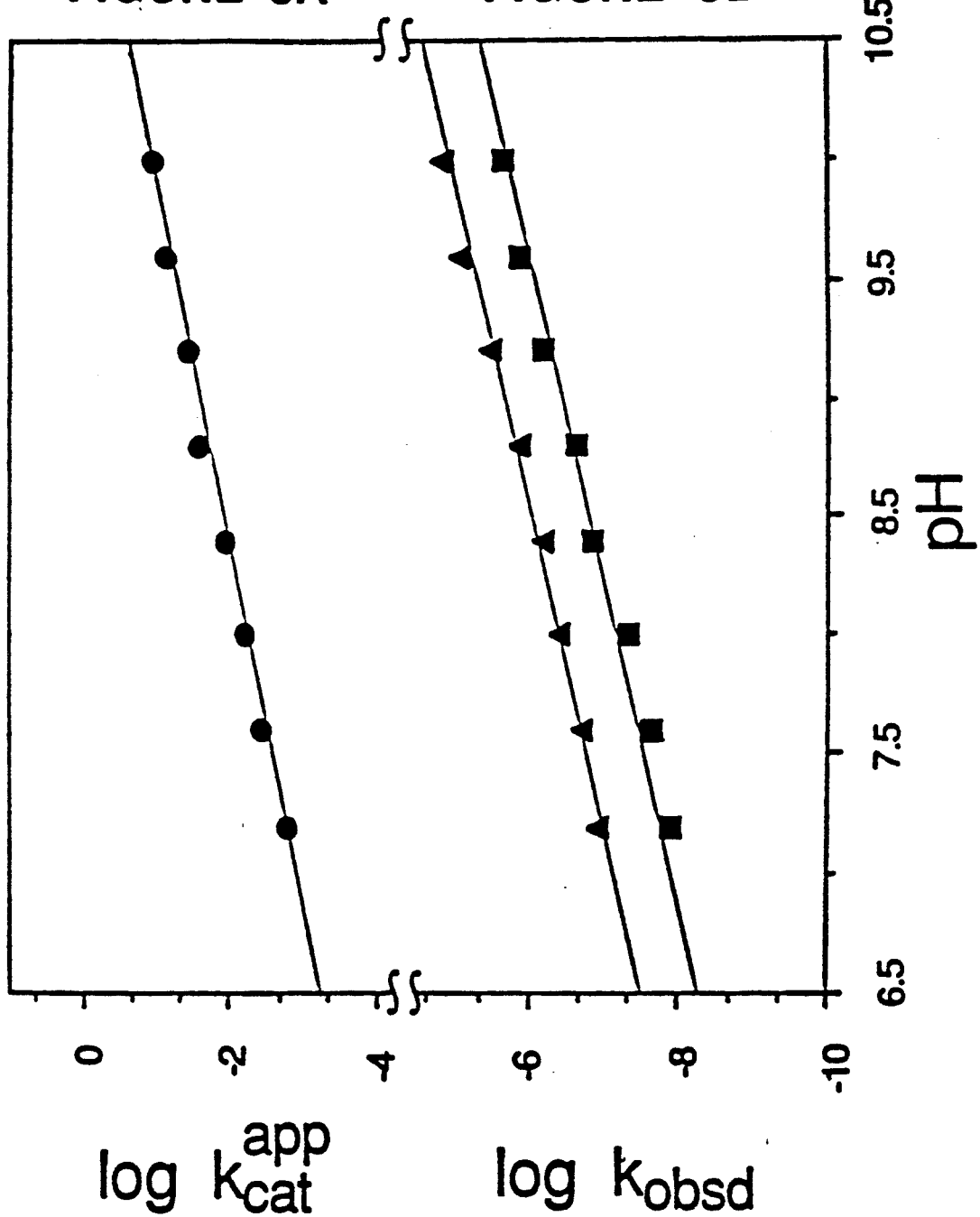

MOLECULES WITH ANTIBODY COMBINING SITES THAT CATALYZE HYDROLYSIS REACTIONS THROUGH USE OF A CHARGED HAPTEN

This invention was made with the support of the U.S. Government, and the U.S. Government has certain rights in the invention.

Cross-Reference to Related Application

This is a continuation-in-part of co-pending U.S. application Ser. No. 470,924, filed Jan. 26, 1990, whose disclosures are incorporated herein by reference

Description

1. Technical Field

The present invention relates to antibodies, antigens and immunogens, and more particularly to molecules that contain an antibody combining site that binds the tetrahedral carbon atom or an amide or ester hydrolysis transition state and surrounding structures, and further provides a site for acid-base or nucleophilic catalysis of the amide or ester bond that is hydrolyzed.

2. Background of the Invention

Binding phenomena between ligands and receptors play many crucial roles in biological systems. Exemplary of such phenomena are the binding of oxygen molecules to deoxyhemoglobin to form oxyhemoglobin, and the binding of a substrate to an enzyme that acts upon it such as between a protein and a protease like trypsin. Still further examples of biological binding phenomena include the binding of an antigen to an antibody, and the binding of complement component C3 to the so-called CR1 receptor.

Many drugs and other therapeutic agents are also believed to be dependent upon binding phenomena. For example, opiates such as morphine are reported to bind to specific receptors in the brain. Opiate agonists and antagonists are reported to compete with drugs like morphine for those binding sites.

Ligands such as man-made drugs, like morphine and its derivatives, and those that are naturally present in biological systems such as endorphins and hormones bind to receptors that are naturally present in biological systems, and will be treated together herein. Such binding may lead to a number of the phenomena of biology, including particularly the hydrolysis of amide and ester bonds as where proteins are hydrolyzed into constituent polypeptides by an enzyme such as trypsin or papain, or where a fat is cleaved into glycerine and three carboxylic acids, respectively.

Slobin, Biochemistry, 5:2836-2844 (1966) reported preparing antibodies to a p-nitrocarbobenzoxy conjugate of bovine serum albumin. Those antibodies were thereafter used to hydrolyze p-nitrophenyl acetate and epsilon-aminocaproate esters. The reaction of the acetate ester was described by a second-order rate constant and was said to appear to be nonspecific. The second-order rate constant obtained using normal gamma globulin was said to be about equal to that of the specially prepared antibodies. The presence of the specially prepared antibodies was said to inhibit the hydrolysis of the aminocaproate ester.

Kohen and co-workers also reported attempts using antibodies to catalyze esterolysis. The antibodies utilized by this group were, in each instance, raised to a portion of the ultimately utilized substrate molecule that did not contain the bond to be hydrolyzed.

In their initial work [FEBS Letters, 100:137-140 (1979) and Biochim. Biophys. Acta, 629:328-337 (1980)] anti-steroid antibodies were used to hydrolyze 7-umbelliferone (7-hydroxycoumarin) esters of a carboxyethyl thioether of a steroid. In each instance, an increase in hydrolytic rate was observed as compared to background or to a rate obtained with normal IgG. In both instances, turn over numbers were low (about one mole of substrates per mole of antibody per minute, or less), and the reaction rates declined with time, reaching a plateau with saturation of the antibody. That slow down in rate was attributed to an irreversible binding of the steroidal acid product to the antibody.

Kohen et al. also reported hydrolyses of 7-[-N-(2,4-dinitrophenyl)-6-aminohexanoyl]-coumarin using monoclonal antibodies raised to the dinitrophenyl portions of that substrate molecule [FEBS Letters, 111:427-431 (1980)]. Here, a rate increase over background was also reported, but the reaction was said to be stoichiometric rather than catalytic. A decrease in rate that approached zero was reported as saturation of the antibody was reached. Again, the decrease was attributed to product inhibition caused by binding of the product acid to the antibody since some of the initial hydrolysis activity could be regenerated by chromatography of an antibody-substrate-product mixture.

When strong antibody binding is directed to stable states of substrate molecules, the slow rate of dissociation of the complex will impede catalysis. Such is thought to be the situation for the results reported by Kohen and co-workers.

The above constructs, though interesting, are severely limited by the failure to address the mechanism of binding energy utilization which is essential to enzymes [W. P. Jencks, *Adv. Enzymol.*, 43, 219 (1975].

Those deficiencies may be redressed by using a transition state analog as the hapten to elicit the desired antibodies. This hapten can assume the role of an inhibitor in the catalytic system.

Thus, immunological binding may be used to experimentally divert binding interactions to catalytic processes. For example, it was suggested that use of an antibody to a haptenic group that resembles the transition state of a given reaction should cause an acceleration in substrate reaction by forcing substrates to resemble the transition state. Jencks, W. P., *Catalysis in Chemistry and Enzymology*, page 288 (McGraw-Hill, New York 1969). Notwithstanding that broad suggestion, specific transition state haptens were not suggested, nor were specific reactions suggested in which the concept might be tested.

Hydrolysis of amide and ester bonds is thought by presently accepted chemical theory to proceed in aqueous media by a reaction at the carbonyl carbon atom to form a transition state that contains a tetrahedral carbon atom bonded to (a) a carbon atom of the acid portion of the amide or ester, (b) two oxygen atoms, one being from the carbonyl group and the other from a hydroxyl ion or water molecule of the medium, and (c) the oxygen atom of the alcohol portion of an ester or the nitrogen atom of the amine portion of an amide. Transition states of such reactions are useful mental constructs that by definition, cannot be isolated, as compared to intermediates, which are isolatable. Although the above hydrolytic transition states cannot be isolated, a large amount of scientific literature has been devoted to the subject.

Whereas the before-described transition state for amide and ester hydrolyses is believed to be well understood, the parameters of the topology, e.g., size, shape and charge, of receptor binding sites in which particular amides, such as proteins, or esters, such as fats, react through those transition states is not as well understood. It would therefore be beneficial if the topology of a plurality of binding sites were known so that the interactions of the ligands that bind in those sites could be studied. Unfortunately, the topology of receptor binding sites in biological hydrolyses is generally unknown, except for a relatively small number of enzymes whose X-ray crystal structures have been determined.

This lack of knowledge of binding site topology stems in part from a lack of knowledge of even the location in cells of many binding sites of receptors. In addition, for those receptor binding sites whose location is known, the chemical identity; i.e., protein and carbohydrate composition, of the binding site is generally unknown. Thus, the investigator is generally stymied in seeking to understand the topological requirements of receptor binding sites and therefore in seeking to construct therapeutic agents that can fulfill those requirements.

Investigators must therefore screen potential therapeutic agents in animal or cell culture studies to ascertain whether a potential therapeutic agent may be useful. Such systems, while useful, are expensive and time-consuming to use.

Even where the topology and chemical reactivity of a hydrolytic receptor such as an enzyme are known, enzymes such as hydrolytic proteases typically cleave their substrates, polypeptide chains, adjacent to a particular amino acid residue that may occur several times in the polypeptide chain of the protein. While such relatively random cleavage can be useful in obtaining a polypeptide map of the protein, that relatively random cleavage is not as useful where particular amino acid residue sequences are desired to be produced.

For example, modern genetic engineering techniques have been useful in preparing fusion proteins that contain a desired protein or polypeptide fused to the transcription product of a vector gene such as the lac z gene. The use of such fusion proteins is, however, hindered by the presence of fragments of the vector gene product. It would also therefore be beneficial if proteolytic enzyme-like molecules could be developed that would cleave such fusion products between the wanted and unwanted fusion polypeptide or protein portions.

Recently, Lerner, Tramontano and Janda [Science, 234, 1566 (1986)] reported monoclonal antibodies that catalytically hydrolyzed an ester. Tramontano and Lerner, also describe using monoclonal antibodies to hydrolyze esters in U.S. Pat. No. 4,656,567. Pollack, Jacobs and Schultz [Science, 234, 1570 (1986)] reported a myeloma protein denominated MOPC167 [Leon et al., Biochem., 10, 1424 (1971)] that catalyzes the hydrolysis of a carbonate.

In the two Lerner and Tramontano disclosures, the antibodies were raised to a phosphonate that was synthesized to represent a stable analog of the tetrahedral hydrolytic transition state of the carboxylic acid ester or carbonate ester. The Pollack et al. antibody principally discussed was a myeloma protein that happened to bind to a phosphonate that was structurally analogous to the carbonate analog hydrolyzed.

Thus, in the Lerner and Tramontano et al. work, the substrate to be hydrolyzed was preselected, with the immunizing analog and hydrolytic antibodies being synthesized in accordance with the desired product. Pollack et al. designed the substrate to be hydrolyzed once they knew the specificity of the myeloma protein. Pollack et al. also reported (above) the existence of a catalytic antibody, substrate and analog substrate system for carbonate hydrolysis similar in concept to that of Lerner et al. Work relating to that system is reported in Jacobs et al., J. Am. Chem. Soc., 109, 2174 (1987).

Published patent application WO 85/02414 discusses the possible use of antibodies as catalysts, and presents data relating to the use of polyclonal serum in hydrolyzing o-nitrophenyl-beta-D-galactoside. The antibodies useful in that application are said to be inducible by a reactant, a reaction intermediate or to an analog of the reactant, product or reaction intermediate. The term "analog" is there defined to encompass isomers, homologs or other compounds sufficiently resembling the reactant in terms of chemical structure that an antibody raised to an analog can participate in an immunological reaction with the reactant but will not necessarily catalyze a reaction of the analog.

The data provided in that specification only indicate that some cleavage of the substrate (reactant) galactoside occurred over an eighteen hour time period using a relatively concentrated antibody preparation (1:10 and 1:20 dilutions). Although catalysis was alleged, catalytic activity was not shown since no turn over of the allegedly catalytic antibody was shown, nor was there an indication of the percentage of substrate galactoside cleaved. That application did indicate that beta-D-galactosidase cleaved about ten times as much substrate as did the polyclonal antibodies, presuming linearity of absorbance at the unnamed concentration of substrate studied.

From the data presented in that application, it is possible that a nucleophilic replacement of the o-nitrophenyl group occurred by a terminal amino group of a lysine residue of the antibody preparation used. Thus, the observed absorbance could have been due to formation of epsilon-amino lysinyl o-nitrophenyl aniline or to the formation of an epsilon-amino-lysinyl galactoside and o-nitrophenol, either of which occurrences would not be catalytic since the antibody was consumed, rather than turning over.

U.S. Pat. No. 4,792,446 to Kim et al. teaches the production of antibody catalysts. Those catalysts react with a substrate and are elicited by a hapten molecule, with the substrate and hapten molecules having substantial structural similarity in portions other than at the atom or group at which the catalytic reaction takes place; i.e., the reaction site. At the reaction site, the substrate and hapten differ in that the reaction site or catalytically active nuclei of the hapten contains a higher valence and one or more bonds than does the analogous structure of the substrate.

Additionally, the hapten includes a group that is bonded to the catalytically active portion of the molecule; i.e., to the structurally analogous portion of the reactive site of the substrate. That added group is said to be useful for introducing into the catalyst antibody a plus ionic charge as with a —$CO_2^-$ group or a minus ionic charge as with an ammonium ion. That added group is also said to replace the —OH of the substrate, to create polar environments, to create non-polar environments or to provide a cavity for water.

Lerner et al., *BioAssays*, 9:107-112 (1988) also teach the use of an ionically charged group of an immunizing hapten to induce the presence of an oppositely charged group in the antibody combining site so that acid-base catalysis can be facilitated using an uncharged substrate. This strategy for inducing catalytic antibodies is referred to therein as "bait and witch" in that the catalytic antibody is induced or baited with a charged hapten and the substrate for the induced antibody catalyst is switched to a neutral molecule so that the complementary ionic charge induced in the antibody to the ionic charge of the hapten can be utilized to provide acid-base catalysis of a reaction of the neutral substrate. No specific haptenic structures are, however, taught for carrying out the "bait and switch" strategy.

BRIEF SUMMARY OF THE INVENTION

The present invention contemplates an antibody molecule or molecule containing antibody combining site portion (catalytic molecule) that catalytically hydrolyzes a preselected carboxylic acid amide or ester bond of a reactant ligand, methods for preparation and use of such molecule, and cells that produce the catalyst molecule.

The catalytically active molecules are preferably monoclonal antibody molecules or molecules containing monoclonal antibody combining site portions. The antibody combining site of those molecules immunoreacts (binds to) at least two ligand molecules. A first ligand molecule is a reactant ligand that contains the preselected carboxylic acid amide or ester bond that is hydrolyzed, as well as a carbon-containing chemical residue bonded to each of the carboxylic acid and amine or alcohol portions of the bond that is hydrolyzed.

A second ligand is a haptenic ligand used directly or indirectly to induce the catalytic molecules. The haptenic ligand is structurally analogous to the reactant ligand, and contains a tetrahedral carbon atom bonded to a hydroxyl group and to a saturated carbon atom at a position in the haptenic ligand corresponding to the position of the carbonyl group and to the carbonyl-bonded heteroatom, respectively, of the preselected reactant ligand carboxylic acid amide or ester to be hydrolyzed. Thus, for example when an amide

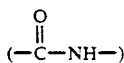

or ester

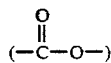

bond is to be hydrolyzed in the reactant ligand, the haptenic ligand contains a

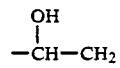

group at a position analogous to the ester or amide bon-d-containing group. Carbon-containing chemical residues bonded to the tetrahedral carbon atom and to the saturated carbon atom of the hapten are structurally analogous (similar) to the chemical residues bonded to the carboxyl portion and the amine or alcohol portion, respectively, of the reactant ligand.

A haptenic ligand also contains a group that bears an ionic charge in aqueous solution at physiological pH values. That ionic charge-bearing group is absent from a corresponding position of the reactant ligand and is located within a spherical volume defined by a radius of about 7, and more preferably about 2 to about 5, Ångstroms from the before-mentioned hydroxyl group-bonded tetrahedral carbon atom. The ionic charge-bearing group preferably provides a carboxylate or ammonium ion in aqueous solution at physiological pH values.

A reactant ligand can be represented by the structure

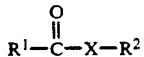

wherein $R^1$ and $R^2$ represent carbon atom-containing chemical residues of the reactant, and —X— is —O— or —NR$^3$—, wherein R$^3$ is hydrogen or a third carbon-containing chemical residue. A haptenic ligand can be represented by the structure

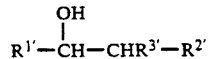

where $R^{1'}$ and $R^{2'}$ represent carbon atom-containing residues that are structurally analogous to $R^1$ and $R^2$, respectively. At least one of $R^{1'}$ and $R'$ contains a group bearing an ionic charge in aqueous solution at physiological pH values, and that ionically charged group is located within a spherical volume defined by a radius of about 7, and preferably about 2 to about 5, Ångstroms from the

group of said structure. $R^{3'}$ is H when —X— is —O—, or $R^{3'}$ is structurally analogous to $R^3$ when —X— is —NR$^3$—.

Cells that produce the above-discussed catalytic molecules when cultured in an appropriate in vivo or in vitro medium are also contemplated. Those cells preferably not only produce the catalytic molecules but also secrete those catalytic molecules into the culture medium. One such preferred cell type is a hybridoma cell.

A method of preparing the above cells is also contemplated. Here, an animal is immunized with an immunogen that includes a before-described haptenic ligand present in an amount sufficient to induce antibodies to the hapten in the animal. The animal is maintained for a time period sufficient for the animal to secrete antibodies that immunoreact with the haptenic ligand.

Genes that encode antibody molecules or molecules containing antibody combining site portions are transferred from antibody-producing cells of the maintained, immunized animal into host cells to form 5 hybrid cells. Those hybrid cells contain genes from at least two sources. When cultured, the hybrid cells produce antibody molecules or molecules containing antibody combining site portions from the transferred genes, and those cells can be cultured substantially indefinitely as compared to the gene transferring antibody-producing cells.

The hybrid cells are cultured in an appropriate medium and under appropriate culture conditions for a time period sufficient for those hybrid cells to produce antibody molecules or molecules containing antibody combining site portions that are recovered and then screened to identify a hybrid cell that produces antibody molecules or molecules containing antibody combining site portions that catalytically hydrolyze the predetermined carboxylic acid amide or ester bond of the reactant ligand. Clones of the identified hybrid cell are then grown.

A method of catalytically hydrolyzing a preselected ester or amide bond in a reactive ligand is also contemplated. Here, a catalytically effective amount of the before-discussed catalytic molecules is admixed with reactant ligand molecules in an aqueous medium to form a reaction mixture. The reaction mixture is maintained for a period of time sufficient for the reactant ligand molecules to bind to the catalytic molecules, and for the catalytic molecules to catalytically hydrolyze the preselected bond and form hydrolysis products. One or more formed products can thereafter be recovered.

BRIEF DESCRIPTION OF THE DRAWINGS

In the drawings forming a portion of this disclosure,

FIG. 2 is a graph showing two pH vs. log K values. The upper portion (FIG. 2A) illustrates a plot of log $k_{cat}^{app}$ vs. pH for log values between $-3$ and $-2$ (solid circles) for the reaction of the monoclonal antibody 30C6 catalyzed reaction of reactant ligand Compound 3. The line through the points was calculated using the equation $$k_{cat}^{app} = (k_{cat}) \frac{K_a}{K_a + a_H}.$$

Figure 1B:
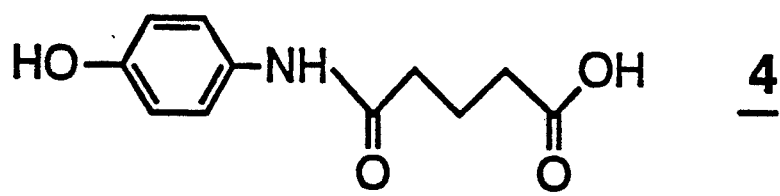
FIG. 1, shown in two sheets as FIG. 1A and FIG. 1B, illustrates the structural formulas of specific haptenic ligands (Compounds 1a, 2, 5a, 6 and 7), an inhibitor (Compound 1bb), substrate or reactant ligand (Compound 3) and the reaction product Compound 4 discussed and utilized herein.

The lower portion (FIG. 2B) shows a plot of log $k_{obs}^c$ vs. pH for log values between $-9.5$ and $-7.0$ (solid triangles) for the reaction of Compound 3 extrapolated to zero buffer concentration. The calculated line was obtained using the equation $$K_{obs}^c = K_o + H_{OH} - [OH^-].$$

pH Values for both plots are between 5.5 and 8.5. Values for the $k_{cat}$, $K_a$ (pK$_a$), $k_o$ and $k_{OH}$ are provided in the Results section hereinafter.

FIG. 3 is a graph in two parts similar to that of FIG. 2. The upper portion (FIG. 3A) illustrates a plot of log $k_{cat}^{app}$ vs. pH for log values between about $-3$ and about $-1$ (solid circles) for the reaction of the monoclonal antibody 27A6 catalyzed reaction of reactant ligand Compound 3.

The lower portion of FIG. 3 (FIG. 3B) shows plots of log $k_{obed}$ (the observed rate constant) vs. pH for log values of about $-8$ to about $-6$ (solid triangles) for the hydrolysis reaction of Compund 3 catalyzed by monoclonal antibody 27A6. The solid squares relate to the log $k_{obed}$ vs. pH for the same reaction extrapolated to zero buffer concentration. The calculated line was obtained using the equation $$k_{obed} = k_{OH} \cdot [OH^-].$$

DETAILED DESCRIPTION OF THE INVENTION

I. Introduction

The present invention relates to antibody molecules or molecules containing antibody combining site portions thereof that can collectively be referred to as receptors or catalytic molecules that are induced by a haptenic ligand analogous in structure to a reactant ligand. The haptenic ligand sterically mimics the conformation but not the ionic charge of a transition state in the reaction sequence for the hydrolysis of an ester or an amide bond of the reactant ligand. The catalytic molecules [antibody molecules or molecules containing antibody combining site (paratopic) portions] bind to the haptenic ligand and to the reactant ligand. The catalytic molecules are thought to stabilize the hydrolytic transition state of a preselected portion of the reactant ligand, as well as providing an ionically charged amino acid residue that contributes acid-base or nucleophilic catalysis for the catalyzed hydrolysis reaction. These molecules catalytically hydrolyze the reactant ligand.

Antibodies and enzymes are both proteins whose function depends on their ability to bind specific target molecules. Enzymatic reactions differ from immunological reactions in that in a enzymatic reaction, the binding of the enzyme to its substrate typically leads to chemical catalysis, whereas a non-catalytic complex is the usual result of antibody-antigen binding.

Enzymes are believed to catalyze the hydrolysis of proteins by combining with the protein to stabilize the transition state of the hydrolysis reaction. It is generally believed that the rate of an enzymatic reaction is increased relative to the rate of a non-enzymatic reaction because of the ability of the enzyme to stabilize the transition state of the reaction; i.e., to reduce the free energy of the transition state, and thus, the free energy of activation, of the reaction [Jencks, W. P., Adv. Enzymology, 43, 219 (1975) and Pauling, L., Amer. Scientist, 36, 58 (1948)]. Support for this theory comes from the observation that substances that are thought to model the presumed transition states are often strongly bound to the enzymes as competitive inhibitors. Leinhard, G., Science, 180, 149 (1973) and Wolfenden, R., Acc. Chem. Res., 5, 10 (1972). It is further thought that the enzyme accomplishes this lowering of the reaction free energy by binding the transition state geometry of the reactant more strongly than it binds to the corresponding substrate(s) or product(s).

This means that the intrinsic binding energy of the enzyme is much greater than can be measured from the binding of substrates or products. Essentially, the binding energy of the enzyme is utilized to perform the chemical reaction [Jencks, W. P., XVII International Solvay Conference (November 1983)].

The converse proposition is that an antibody that is prepared to optimally bind a suitable mimic of a transition state would function as a catalyst. The demonstration of this result completes the correlation of enzyme function and antibody structure and provides a useful approach to devising artificial enzymes.

The basic idea behind immunological hydrolysis described herein contemplates the use of a haptenic ligand in the induction of antibodies of predetermined specificity that (a) preferentially bind to and thereby stabilize the transition state of amide or ester bond hydrolysis upon binding to the specified reactant ligand and (b) presumably provide an ionically charged acid-base or nucleophilic reaction-catalyzing amino acid residue in the induced combining site. A haptenic ligand useful herein simulates the conformation but not the ionic charge of a high energy transition state in amide or ester hydrolysis to induce the production of antibodies having the ability to bind related substrates (reactant ligands) and stabilize their hydrolyses. The haptenic ligand also includes a group that provides an ionic charge in aqueous solution at physiological pH values to induce an oppositely charged amino acid residue in the antibody combining site. That oppositely charged amino acid residue is believed to provide the acid-base or nucleophilic reaction catalytic effect.

Such preferential binding and stabilization results in a reduction in the activation energy for the hydrolysis reaction, thus meeting a criterion for catalysis. The presence of a charged amino acid residue in the combining site can mimic the charged residues present at the active sites of proteolytic enzymes such as the serine proteases. Antibodies that display this property can be obtained by immunization with synthetic haptens that are chemically modified to induce a charged residue as well as to resemble the bonding characteristics of a substrate reactant ligand undergoing bond hydrolysis; i.e., by immunization with a transition state steric mimic of the particular reaction.

Monoclonal antibodies have been shown to catalyze a variety of acyl transfer reactions [(a) Tramontano et al. *Proc. Natl. Acad. Sci. USA*, 83:6736 (1986); (b) Tramontano et al. *Science*. 234:1566 (1986); (c) Jacobs et al., *J. Am. Chem. Soc.*, 109:2174 (1987); (d) Mapper et al., *Science*, 237:1041 (1987); (e) Janda et al., *Am. Chem. Soc.*, 110:4835 (1988); (f) Janda et al., *Science*, 241:1199 (1988); (g) Janda et al., *Science*. 244:437 (1989)], by utilizing haptenic transition-state models, [(Lerner et al., *BioAssays*. 9:107–122 (1988)].

In order to expand the scope and capabilities of these hydrolytic antibodies or receptors, also referred to as abzymes, new strategies must be developed for eliciting catalytic activity in the combining sites of antibodies. Recent reports have focused attention on the modification of an antibody's binding pocket or site through either semi-synthetic methods [(a) Pollack et al., *Science*, 242:1038 (1988) (b) Pollack et al., *J. Am. Chem. Soc.*, 111:1929 (1989)] or site-directed mutagenesis [Baldwin et al., *Science*, 245:1104 (1989)]. However, the generality of such strategies may be reduced because of the lack of available structural data for catalytic antibodies.

It was felt that a process that could induce catalytically active groups de novo from a haptenic antigen might prove more advantageous because one can harness the vast variability of the immune response, via the somatic mutation process, to perform "in vivo" mutagenesis. The Results discussed hereinafter report a tactic that elicits an amino acid residue(s) within the binding site of the induced antibody molecule to assist in any acyl transfer reaction by a methodology previously termed the "bait and switch" catalysis.

Figure 1B:
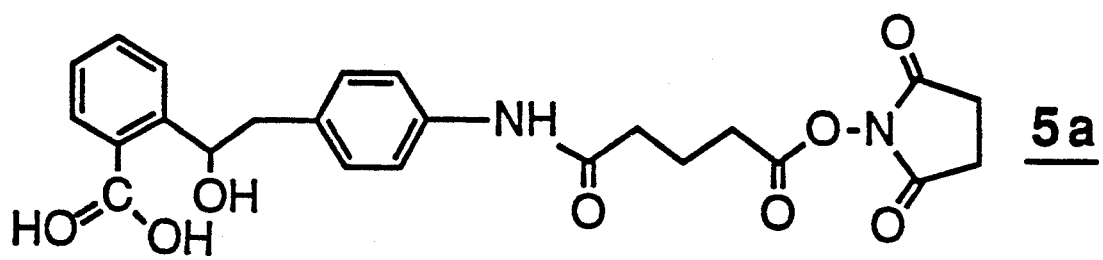
Figure 1B:
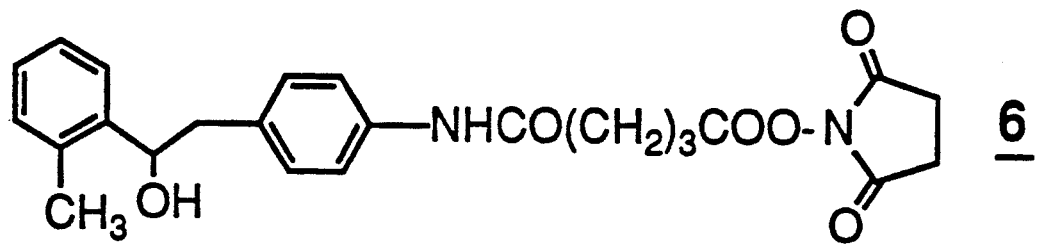
Figure 1B:
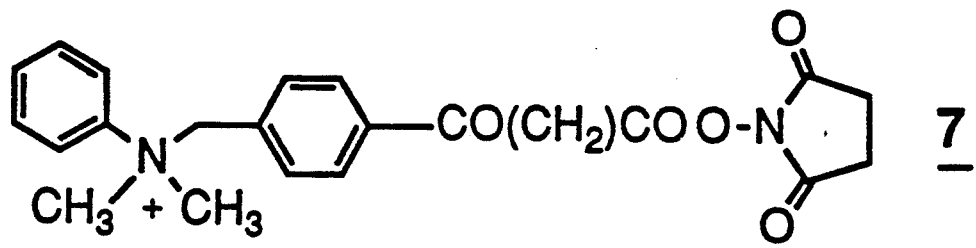

The plan here involved the placement of an ionic charge within the antigen or haptenic ligand Compound 1a, (FIG. 1) in close proximity to the acyl moiety to be hydrolyzed. The antibodies raised to this hapten are presumed to possess amino acid residue(s) at the combining site having a charge complementary to this haptenic charge [(a) Pressman et al., *J. Am. Chem. Soc.*, 68:250 (1946); (b) Pressman et al., *J. Am. Chem. Soc.*, 75:686 (1953); (c) Grossberg et al., *J. Am. Chem. Soc.*, 82:5470 (1960); (d) Shokat et al., Nature (London), 338; 269 (1989)].

In addition, Compound 1a presents to the antibody a hydroxylic group having a tetrahedral geometry that serves as a steric mimic or representation of the acyl transfer transition state. This position was kept uncharged so that there would be no additional electrostatic effects.

The benzoate substrate or reactant ligand Compound 3 (FIG. 1) corresponding to hapten Compound 1a has similar steric dimensions (determined from MM2 calculations), but lacks the positive charge. Hence, the ionically charged amino acid residue presumed to be at the induced catalytic antibody combining site is freed from ion pair formation and serves as a potential general acid-base or nucleophilic catalyst.

The pyridine haptenic ligand Compound 2 (FIG. 1), functions as a control, since it is structurally identical to Compound 1a, but lacks the methyl group and a charge at physiological pH values. Charge complementarity has been previously employed to abstract a substrate proton in an antibody catalyzed $\beta$-elimination reaction, although no comparison was made to a neutral hapten. Shokat et al., *Nature* (London). 338:269 (1989).

The term "receptor" is used herein to mean a biologically active molecule that binds to a reactant ligand, inhibitor ligand, or haptenic ligand. The receptor (catalytic) molecules of the present invention are antibodies, substantially intact antibodies or idiotype-containing polyamide (paratope-containing) portions of an antibody.

Biological activity of a receptor molecule is evidenced by the binding of the receptor to its antigenic reactant ligand, inhibitor ligand or haptenic ligand upon their admixture in an aqueous medium, at least at physiological pH values and ionic strengths. Preferably, the receptors also bind to an antigenic ligand within a pH value range of about 5 to about 9, and at ionic strengths such as that of distilled water to that of about one molar sodium chloride.

Idiotype-containing polyamide portions (antibody combining sites or paratopes) of antibodies are those portions of antibody molecules that include the idiotype, and bind to the reactant ligand or haptenic ligand. Such portions include the Fab, Fab' and F(ab')$_2$ fragments prepared from antibodies by well-known enzymatic cleavage techniques. See for example, U.S. Pat. No. 4,342,566 to Theofilopoulos and Dixon, generally, and specifically, Pollack et al. [*Science*. 234, 1570 (1987)] who reported accelerated hydrolytic rates for Fab fragments were the same as those of the native Ig. Inasmuch as the antibodies from which idiotype-containing polyamides are obtained are described as raised against or induced by immunogens, idiotype-containing polyamide receptors are discussed as being "raised" or "induced" with the understanding that a cleavage step is typically required to obtain an idiotype-containing polyamide from an antibody. Intact antibodies are preferred, however, and are utilized as illustrative of the receptor molecules of this invention.

The receptors (catalytic molecules) useful in the present invention are preferably monoclonal antibodies or portions thereof. A "monoclonal antibody" is a receptor produced by clones of a single cell that produces, and often secretes, but one kind of receptor molecule. The hybridoma cell is an example of such a cell, and is fused from an antibody-producing cell and a myeloma cell or other self-perpetuating cell line.

Techniques for preparing the monoclonal antibodies of the present invention using hybridoma technology are well known. Such receptors were first described by Kohler and Milstein, *Nature.* 256, 495 (1975), which is incorporated herein by reference. Monoclonal antibodies are typically obtained from hybridoma tissue cultures or from ascites fluid obtained from mammals into which the hybridoma tissue was introduced. Both methods are described herein.

Monoclonal catalytic molecules are preferred herein because of their unique specificity in binding to a particular epitope such as a particular immunizing haptenic ligand and reactant ligand, as well as their relatively higher specific catalytic activity as compared to polyclonal antibodies. Polyclonal antibody preparations can also be used herein, but typically have to be separated into fractions that bind to the immunizing haptenic ligand and those that bind to extraneous epitopes such as those of the antigenic carrier.

Polyclonal antibodies that bind to the haptenic ligand can be separated by affinity separation using an haptenic ligand as the affinity sorbant. After admixture and maintenance of an antibody preparation with the affinity sorbant for a time sufficient for appropriate immunoreaction to take place, the affinity sorbant is separated from the remaining portion of the antibody preparation.

The separated, remaining antibody portion bound to the affinity sorbant contains the antibodies that bind to the haptenic ligand, whereas antibodies in the separated remaining portion of the antibody preparation bind to extraneous epitopes. Those affinity-bound antibodies can thereafter be isolated by usual techniques for separating bound entities from affinity sorbants, such as washing the sorbant with glycine-hydrochloride at pH 2.

A "ligand" is defined herein as a molecule or complex that immunoreacts with or binds to a receptor molecule antibody combining site. Two principal types of ligand are contemplated herein. A first is termed a haptenic ligand and is used as an immunogen to induce preparation of receptor molecules, as an inhibitor of the receptor molecule-catalyzed reaction and as an antigen in ELISA or other assays. The second is referred to as the reactant ligand or substrate and is the molecule that undergoes the catalyzed reaction. The haptenic ligand is substantially inert to undergoing the catalyzed reaction.

As described herein, chemical analogs of amide or ester reactant ligands have been synthesized as haptens that incorporate a tetrahedral carbon atom bonded directly to a hydroxyl group and also directly to a saturated carbon atom at a specific, predetermined site to mimic the conformation but not the ionic charge of the transition state in the hydrolysis of an amide or ester bond of a structurally similar or analogous reactant ligand.

Hydrolysis of the amide bond of polypeptides or proteins requires haptenic ligands that are substantially free from hydrolysis when utilized as a haptenic immunogen. Thus, a haptenic ligand that includes the tetrahedral carbon, its hydroxyl group and adjacent, directly bonded saturated carbon atom are free from such possible hydrolysis.

Short polypeptide chains can induce the production of antibodies that recognize and bind to a homologous protein at a predetermined specific site. The present invention carries the earlier work With polypeptides a major step forward.

Here, the antibodies (receptors) are induced by an immunizing, ionic charge-bearing haptenic first molecule (the haptenic ligand), and recognize and bind not only to that first molecule, but also to a second, related molecule (the reactant ligand) that is free from an ionic charge at an analogous position. In binding that second molecule, the receptor causes hydrolysis (which as demonstrated herein is catalytic) of a preselected, ester or amide bond that corresponds in topology to the topology of the immunizing, haptenic first molecule. The correspondence in topology; i.e., size and shape but not ionic charge, provides a means for preselecting the site at which hydrolysis of the ligand occurs. Inhibitor ligands that resemble the structure of a haptenic ligand or a reactant ligand are also bound by receptor molecules.

Consequently, by synthesis of a relatively small, immunizing haptenic ligand, one can induce the production of receptor molecules that recognize, bind to and catalytically cleave an ester or amide bond in another molecule that contains a plurality of amide or ester bonds. Thus, receptor molecules can be prepared that catalytically hydrolyze a selected, predetermined amide bond of a protein or polypeptide such as a genetically engineered fusion protein, or an ester bond of a preselected ester in a polyester.

The implication of this result is that one can confer the activity of hitherto unknown proteases and esterases to immunoglobulins.

II. Transition State of Esterolysis and Haptenic Ligand Design

Design of the haptenic ligand flows backward from the structure of the hydrolysis products to be formed, through the transition state for bond breaking to be mimicked, and then to the haptenic ligand. Reactions that involve amide or ester hydrolysis provide illustrative examples of the general concept and are utilized herein as exemplary for an ester or amide hydrolysis reaction.

Transacylation processes are characterized by carbonyl addition-elimination mechanisms. The acyl group may, therefore, possess varying degrees of tetrahedral character in this transition state. W. P. Jencks, *Catalysis in Chemistry and Enzymology*, Ch. 10, (McGraw-Hill, New York, 1969). The enzymes that catalyze transacylation reactions might be expected to bind well those analogs of the reactant ligand having a tetrahedral configuration about the acyl center. This is true for serine proteases, where a covalent bond between the ligand (substrate) and the enzyme is formed temporarily [Westerik et al., *J. Biol. Chem.*, 247, 8195 1972); R. C. Thompson, *Biochemistry*, 12, 47 (1 973) and Imperali et al., *Biochemistry*, 25, 3760 (1986)], as well as for enzymes that catalyze the direct hydration of amides or esters. The latter category is inhibited by compounds with a tetrahedral configuration including a phosphate, phosphonate or phosphonamidate group in lieu of the scissile amide unit [Weaver et al., *J. Mol. Biol.*, 114, 119 (1977) and Jacobsen et al., *J. Am. Chem. Soc.*, 103, 654 (1981].

The hydrolysis of carboxylic acid esters is a simpler example of transacylation that is approximated by the haptenic steric mimic of the transition state. Ester hydrolysis reactions generally proceed at convenient spontaneous rates under ambient conditions that are suitable for antibodies. Therefore, any small rate acceleration can be readily detected.

A useful haptenic ligand contains a tetrahedral carbon atom that is bonded to a hydroxyl group as well as being also bonded directly to a saturated carbon atom. Those atoms sterically mimic the tetrahedral carbon atom and linked oxygen atom or nitrogen atom (heteroatom) of the hydrolytic transition state of a carboxylic acid ester or amide bond, but do not mimic the ionic charge of the transition state. Thus, the tetrahedral carbon atom, its hydroxyl group and directly bonded saturated carbon atom are at a position in the haptenic ligand corresponding to the position of the carbonyl group as well as to the carbonyl-bonded heteroatom (oxygen or nitrogen), respectively, of the preselected carboxylic acid amide or ester bond to be hydrolyzed in the reactant ligand. Carbon atom-containing chemical residues that are structurally analogous to carbon atom-containing residues of the reactant ligand are bonded to the tetrahedral carbon atom and to the saturated carbon atom so that the haptenic and reactant ligands are structurally similar or analogous except at the atoms at which hydrolysis takes place.

This structural steric mimic of the reactive carbonyl and oxygen or nitrogen atom thus differs from the phosphonate or phosphonamidate groups or the carbonate group used by previous workers as analogous to the hydrolytic transition state. The present steric mimic also differs from the groups discussed in the Kim et al. patent in that the structure in a present hapten contains a lower valence than the analogous structure in the substrate and contains the same number of bonds, not more than the analogous structure of the substrate.

A hapten useful herein further includes a group that bears an ionic charge in aqueous solution at physiological pH values. That ionic charge-bearing group can be bonded directly to the above-mentioned tetrahedral carbon atom. Preferably, however, the ionic charge-bearing group is indirectly bonded to the tetrahedral carbon atom and is located within a spherical volume defined by a radius of about 7 Ångstroms (Å) from the tetrahedral carbon atom. More preferably, that radius is about 2 to about 5 Å.

The ionic charge-bearing group is absent from a corresponding position in the reactant ligand or substrate, and can be selected from a number of well known groups.

For example, groups bearing a negative charge at physiological pH values, for inducing a complementary positive charge in the antibody combining site, include carboxyl (—$COH_2$), phosphono [—$P(OH)_2O$], sulfo (—$SO_3H$), phosphoro [—$OP(OH)O$], sulfato (—$OSO_3H$), and the like. Exemplary groups that bear a positive ionic charge at physiological pH values, for inducing a complementary negative charge in the antibody combining site, include amino (—$NH_2$), guanidine [—$HNC(N)NH_2$], mono- and di-substituted amino where each substituent contains up to about ten carbon atoms such as $C_1$-$C_6$ lower alkyl, benzyl, phenyl and naphthyl, or where two substituents form a five- or six-membered ring as in morpholine, piperidine, pyrrolidine, substituted guanidine compounds having the above substituents, and quaternary nitrogen-containing groups such as tri-substituted ammonium compounds like the triethyl ammonium group or a quaternized aromatic ring such as a substituted quinolinium or pyridinium ring. Each of the above neutrally charged groups exists as a negatively or positively charge ionic group in aqueous solution at physiological pH values.

Carboxyl groups and quaternary amines as are found in heteroaromatic rings that provide carboxylate and ammonium ions are preferred. Quaternary amines, whether quaternized by four substituent groups or by protonation, and whether present in acyclic form or in cyclic form as part of a ring such as in an N-methyl pyridinium residue, are all considered to be in the class of ammonium groups when ionic charge-bearing groups are discussed.

Where the group that bears an ionic charge at physiological pH values is part of another group that is bonded to the before-mentioned tetrahedral carbon atom as is the case of the quaternary nitrogen atom of the N-methyl pyridinium compound used illustratively herein in Compound 1a, the ionic charge-bearing group is considered to be the quaternary nitrogen atom of the pyridinium ring. The ionic charge-bearing group in such a structure is thus bonded indirectly to the tetrahedral carbon atom, and the atom of that ionic charge-bearing group that bears the ionic charge; i.e., a quaternary nitrogen atom, is separated from that tetrahedral carbon atom by at least one atom, preferably a carbon atom. A molecule such as a glycolic acid derivative contains the ionic group bonded directly to the tetrahedral carbon atom and its hydroxyl group.

The reactant ligand is structurally analogous (similar) to the haptenic ligand and vice versa, but a reactant ligand is free from the before-discussed group bearing an ionic charge in aqueous solution at physiological pH values that is located in a position structurally analogous to the location of that group in the haptenic ligand. Thus, illustrative haptenic ligand Compound 1a contains N-methyl pyridinium quaternary nitrogen, whereas the illustrative substrate ligand Compound 3 contains a neutrally charged phenyl ring and its carbon and hydrogen atoms at the corresponding position.

The haptenic ligand and/or the reactant ligand (substrate) can also include one or more additional groups that bear an ionic charge in aqueous solution at physiological pH values. Those ionic charge-bearing groups can be in corresponding or non-corresponding locations in the two types of ligand molecules. In addition, such an additional ionically charged group can exist within the same spherical volume defined for the before-described ionic charge-bearing group.

The presence in one or the other or both the haptenic ligand and reactant ligand of one or more ionically charged groups in addition to the at least one such ionically charged group discussed previously can also be useful to facilitate binding of a hapten to the combining site of the catalyst molecule. This is particularly the case where a relatively small hapten such as those used illustratively herein is utilized.

For example, studies with dextrans have shown that maximal binding of anti-dextran antibodies occurs with dextrans containing six or seven glucose residues. Studies with polyalanine oligomers have shown maximal binding at a size of four to six amino acid residues. Chapman et al., *Microbiology*, 2nd ed., Chapter 16, pages 444-447. Smaller oligomers bound less well, with glucose exhibiting no binding.

Thus, providing either or both ligands with one or more added ionic charges can assist binding by the catalytic antibody combining site through charge complementation as well as by structural fit where a ligand is smaller than the full size that can be accommodated by the binding site.

Thus, the haptenic ligand contains at least one group that provides an ionic charge in aqueous solution at physiological pH values such as an amine, quaternary nitrogen atom or carboxyl group that provide an ammonium group or a carboxylate group, respectively. That charged group is within the defined spherical volume, and is absent from a corresponding position in the reactant ligand.

As already noted, the spherical volume within which the at least one ionic charge-bearing group is located in the haptenic ligand is defined by a radius of about 7 Å from the tetrahedral carbon atom, and is more preferably within a volume defined by a radius of about 2 to about 5 Å from that tetrahedral carbon atom. Such spherical volumes and radii can be calculated using computer programs well known in the art or by use of molecular models.

It is to be understood that the placement of that at least one ionic charge-bearing group in the haptenic ligand is such that the presumptively induced complementary charged amino acid residue of the antibody combining site has access to the carbonyl group and its bonded oxygen or nitrogen atoms of the ester or amide to be hydrolyzed. Put differently, the ionic charge-bearing group of the haptenic ligand is not sterically hindered from the tetrahedral carbon atom, its hydroxyl group and adjoining saturated carbon atom.

A useful reactant ligand is represented by the structure

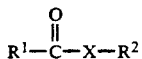

wherein $R^1$ and $R^2$ represent carbon atom-containing chemical residues, and —X— is —O— or —NR$^3$—, where $R^3$ is hydrogen or a third carbon-containing chemical residue.

$R^1$ and $R^2$ can be the same or different. Each group can be an amino acid residue, a polypeptide or protein, as well as an organic radical such as an aliphatic or substituted aliphatic straight or branched open chained or cyclic residue, including a cyclic or open chained heteroatom-containing residue, and can also be an aromatic, substituted aromatic, heteroaromatic or substituted heteroaromatic residue. So long as the reactant ligand can be solubilized in an aqueous medium that does not substantially inhibit the action of the catalyst molecule and is large enough to be bound by the catalyst, the specific structures of $R^1$ and $R^2$ can be substantially any carbon-containing chemical residues.

When other than hydrogen (H), $R^3$ can also be substantially any carbon-containing chemical residue, as was the case with $R^1$ and $R^2$.

A haptenic ligand is structurally analogous (similar) to the reactant ligand. A haptenic ligand is represented by the structure

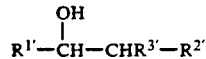

where $R^{1'}$ and $R^{2'}$ represent carbon atom-containing residues that are structurally analogous (similar) to $R^1$ and $R^2$, respectively, and $R^{3'}$ is structurally analogous (similar) to $R^3$ when —X— is —NR$^3$—. When —X— is —O—, $R^{3'}$ is hydrogen. At least one of $R^{1'}$ and $R^{2'}$ also provides the group that bears an ionic charge in aqueous solution at physiological pH values that is absent from the reactant ligand, and that group is within the previously discussed spherical volume.

In preferred practice, the members of the R group pairs $R^1$ and $R^{1'}$, $R^2$ and $R^{2'}$, $R^3$ and $R^{3'}$ are so structurally analogous that $R^1$ and $R^{1'}$ are substantially identical, $R^2$ and $R^{2'}$ are substantially identical and $R^3$ and $R^{3'}$ are substantially identical, except when —X— is —O—. In this preferred situation, the differences between the similarly numbered pairs of R groups is that the haptenic ligand contains the ionic charge-bearing group not present in the reactant ligand, and the haptenic ligand also includes an atom or group that is utilized to link the haptenic ligand to an antigenic (immunogenic) carrier molecule to form an immunogenic conjugate, as is discussed hereinafter.

Thus, except for the above-noted differences, the similarly numbered paired groups are preferably of about the same size, shape, charge and degree of unsaturation. Where the size of the similarly numbered paired R groups differs, it is preferred that the haptenic ligand be of larger size than the reactant ligand so that the smaller reactant ligand can be accommodated within the induced catalytic binding site.

The structures of the illustrative haptenic ligands and reactant ligands utilized for this investigation were selected according to certain criteria. These included the availability and stability of the tetrahedral carbon atom-containing precursors, the corresponding carboxylic acid amide or ester substrate, the convenience of the chemical synthesis for its preparation, and the adaptability to diverse schemes for immunological presentation. By including amino substituents in the aromatic rings, either the benzylic or phenolic group, for example, can be provided with a functional appendage for coupling to immunogenic carrier proteins for haptenic presentation.

III. Catalytic Antibody Producing Cells and Methods

Cells that when cultured in an appropriate medium produce monoclonal catalyst molecules (antibody molecules or molecules containing antibody combining site portions) that catalytically hydrolyze a preselected carboxylic acid amide or ester bond of a reactant ligand are also contemplated herein. Those cells preferably also secrete the above molecules into their culture medium environment, whether that culture medium environment is in vitro or in vivo. In a preferred embodiment, those cells are hybridoma cells, such as hybridoma 30C6.

Generally, such catalyst molecule-producing cells are prepared by immunizing a laboratory animal such as a mouse, rat, goat or horse with an immunogen that contains an antibody-inducing amount of a before-described haptenic ligand. Typically, the immunogen is a conjugate of the haptenic ligand and an antigenic (immunogenic) carrier, as is discussed hereinafter.

The animal so immunized is maintained for a time period sufficient for the animal to secrete antibodies that immunoreact with the haptenic ligand. The ELISA assay discussed hereinafter is useful to determine the presence of a required immunoreaction.

Genes that encode antibody molecules or molecules containing antibody combining site portions thereof from antibody-producing cells of the above-maintained animal such as splenocytes are transferred into host cells. This gene transfer forms hybrid cells that contain genes from at least two sources. The hybrid cells produce the antibody molecules or antibody combining site portions from the transferred genes when appropriately cultured, and can be cultured substantially indefinitely, relative to the antibody-producing cells from which the genes had been transferred. Exemplary cells that can be cultured substantially indefinitely relative to the gene transferring cells include hybridoma cells, *E coli* cells, yeast cells such as *S. cerevisiae*, transformed mammalian cells such as CHO cells and the like.

The hybrid cells so produced are cultured in an appropriate culture medium, e.g., in vivo or in vitro, for a time period sufficient for those cultured hybrid cells to produce antibody molecules or molecules containing antibody combining site portions thereof, which molecules are thereafter recovered. Exemplary in vivo and in vitro culture conditions for hybridoma cells are discussed herein and are well known, as are culture conditions for cells such as *E. coli, S. cerevisiae*, CHO and the like.

The recovered molecules are then screened to identify a hybrid cell that produces molecules that catalytically hydrolyze the predetermined carboxylic acid amide or ester bond of the reactant ligand. Once such a hybrid cell is identified, more clones of that hybrid cell are grown.

The above process encompasses hybridoma preparation, a method well known in the art, and that is discussed in detail herein. It is also known in the art that genes that encode substantially only the antibody combining site portion of an antibody molecule can be transferred from one mammalian cell to another, and the above-described process is also intended to include such processes. The above-described process is also intended to encompass the method of Shastry et al., *Proc. Natl. Acad. Sci., USA*, 86:5728 (1989) and Huse et al., *Science*, 246:1275 (1989), whose disclosures are incorporated by reference, in which molecules containing antibody combining site portions are produced in non-mammalian organisms such as *E. coli* by use of genetic engineering techniques. The transferred genes of those papers resulted from use of mRNA from hybridomas or the spleens of immunized animals to prepare genes encoding $V_H$ or Fab antibody portions, respectively, that were expressed in *E. coli* cells.

In another method aspect of this invention, a catalytic amount of the monoclonal antibody molecules or molecules containing antibody combining site portions thereof (catalytic molecules) produced by such cells are admixed with reactant ligand molecules in an aqueous medium to form a reaction admixture. The reaction admixture so formed is maintained for a time period sufficient for the reactant ligand molecules to bind to the catalytic molecules, and for the catalytic molecules to catalytically hydrolyze the preselected bond. A product of the hydrolysis reaction can be recovered if desired.

This hydrolytic method of this invention utilizes an aqueous medium as a portion of the reaction admixture. That medium typically contains water and buffer salts. In addition, the medium can contain other salts such as sodium chloride, as well as water-soluble calcium and magnesium salts as are frequently found in protein-containing media. Organic solvents such as methanol, ethanol, acetonitrile, dimethyl sulfoxide, dioxane, hexamethylphosphoramide and N,N-dimethylforamide can also be present. Surface active agents that emulsify the reactant ligand and receptor molecule can also be present. The critical feature of ingredients present in the aqueous medium is that those ingredients not substantially interfere with or inhibit the catalytic reaction as by denaturation of the catalytic molecule. Additionally, the aqueous medium is substantially free from salt, proteins generally, and enzymes, specifically, that inhibit the bond-breaking reaction catalyzed by the catalytic molecule.

The aqueous medium typically has a pH value of about 5 to about 9, and preferably about pH 6.0 to about 8.0. pH Values greater and less than those recited values can also be utilized so long as the catalyzed reaction is again not substantially interfered with or inhibited.

The catalytic reactions are typically carried out at ambient room temperature; i.e., at about 20° to about 25°degrees C. or at 37° degrees C., and at an ambient atmospheric pressure; i.e., at about one atmosphere. However, temperatures down to about the freezing point of the aqueous medium and up to about the boiling point of the medium at atmospheric pressure can also be used. As is known, proteins such as the present catalytic molecules tend to denature at elevated temperatures such as those at which an aqueous medium boils, e.g. at about 100° degrees C., and thus temperatures below about 40° degrees C. are preferred.

The reactant ligand is present in a reaction mixture in an amount up to its solubility in the aqueous medium. A two phase system that includes insoluble reactant ligand can also be used, but normally is not so used. Normally used concentrations of the reactant ligand a re about 0.1 micromolar ($\mu$M) to about 10 millimolar (mM), with that amount also being a function of the solubility of the reactant ligand in the aqueous medium. Where the product is desired, per se, relatively higher concentrations are used as compared to lower concentrations where a reaction mechanism or reaction kinetics are to be studied.

A catalytically effective amount of the catalytic molecules is also present. Thus, the catalytic molecules are typically used at a molar ratio to the reactant ligand of about 1:2 to about 1:10,000, with a molar ratio of about 1:10 to about 1:100 being preferred.

The ratio of catalytic molecules to reactant ligand typically depends upon the specific activity of the catalytic molecules toward the reactant ligand and the purpose of the user in running the reaction. Thus, where the product is desired, a relatively higher concentration of catalytic molecules, and a higher catalytic molecules to reactant ligand ratio are used. Where the reaction mechanism or kinetics of the reaction are being studied, a lower concentration and ratio are typically used. A stoichiometric amount of catalytic molecules or less can also be used, but since catalytic molecules are utilized, use of even a stoichiometric amount can be wasteful.

The duration of the reaction maintenance time period is a function of several parameters including the catalytic molecules and reactant ligand selected, their concentrations pH value and temperature, as well as what is being sought from the reaction. Where kinetics studies are being carried out, maintenance times of minutes to hours are frequently encountered. Where the reaction products are desired, maintenance times of hours to days are more usual.

IV. Results

Haptenic ligand Compounds 1a and 2 were synthesized in five and four steps respectively, starting from 4-nitro-phenethylbromide as is described hereinafter. [All new compounds exhibited satisfactory spectroscopic (NMR, IR) and combustion analysis (±0.3 percent)]. Both haptenic ligand Compounds 1a and 2 were coupled (via the N-hydroxysuccinimide ester) to the carrier proteins bovine serum albumin (BSA) and keyhole limpet hemocyanin (KLH) to form immunogenic conjugates. 129G1X. Mice were immunized with the KLH conjugate of Compounds 1a and 2, and antibodies were generated and screened as described elsewhere herein. [(a) Kohler et al., *Nature* (London), 256; 495 (1975); (b) Enguall, *Method Enzymol*, 70:419 (1980)].

Immunization with haptenic ligand Compound 1a produced 23 hybridomas, whereas haptenic ligand Compound 2 yielded 21 hybridomas that bound to the respective haptens. All monoclonals were of the IgG class and were purified from ascites fluid by anion exchange chromatography followed by affinity chromatography on a protein G column. Antibodies were judged to be homogeneous by sodium dodecyl sulfate polyacrylamide gel electrophoresis.

Monoclonal antibodies at a concentration of 20 μM were initially screened (phosphate buffer 50 mM, pH 7.5, 100 mM NaCl, 37° degrees C.) against benzoate ester reactant ligand Compound 3, (500 M) for the production of 5-[[4-(hydroxy)phenyl]amino]-5-oxo-pentanoic acid, Compound 4. [Analysis was performed via HPLC on an RP-C18 column eluting with water: acetonitrile (op:10) at a flow of 1 ml/min with UV detector set to 254 nm. The hydrolysis product, Compound 4 (FIG. 1; retention time 7 minutes) was collected (recovered) an found to be identical by RP-HPLC coinjection and mass spectral analysis with an authentic sample.]

From the twenty-three monoclonal antibodies obtained to haptenic ligand Compound 1a, seven were found to be catalytic. None of the antibodies to haptenic ligand Compound 2 showed any tendency to accelerate the rate of hydrolysis of the reactant ligand ester, Compound 3.

The seven antibodies that were found to be catalytic were completely inhibited by the addition of free hapten Compound 16. Such results suggest catalysis follows binding of the substrate in the antibody binding pocket or combining site.

Most significant was the overwhelming number of catalytic antibodies induced by haptenic ligand Compound 1a vs. Compound 2. One of these seven catalytic antibodies denominated hybridoma and monoclonal antibody 30C6 was characterized in detail.

The initial rate of hydrolysis of substrate or reactant ligand Compound 3 (50 mM phosphate, 100 mM NaCl, pH 7.2, 37° degrees C.) catalyzed by monoclonal antibody 30C6 (20 μM) followed Michaelis-Menten kinetics [concentrations of hydrolysis product Compound 4 were determined by HPLC measurements of its peak height relative to that of an internal standard over 1-2 hours (3 or more determinations).]A standard curve showed linearity with concentrations of hydrolysis product Compound 4 up to 0.5 mM) with values of $K_{cat}^{app}$ and $K_m$, of $5\pm0.2\times10^{-3}$ min$^{-1}$ and $1.12\pm0.05$ mM, respectively. The antibody-catalyzed hydrolysis of benzoate reactant ligand Compound 3 was competitively inhibited (K:=83±5 μM) by the addition of pyridinium salt Compound 1b.

The pH dependence of the hydrolysis of substrate Compound 3 was examined in the presence of monoclonal antibodies 30C6 (20 μM) between pH 6.0 and 7.2 (Bis-tris) and 7.2–8.0 (phosphate), both at 50 mM buffer and 100 mM NaCl, 37° degrees C. (FIG. 2). The pH dependence of $K_{cat}^{app}$ reveals participation by the basic form of a dissociable group, whose $pK_a$ was determined to be 6.26±0.05 (FIG. 2A) Variation of the buffer ion concentration (12.5-50 mM) showed no dependency of $k_{cat}$ on the presence of buffer species.

For direct comparison, the rates of hydrolysis ($K_{obs}^c$) of reactant ligand Compound 3 over the identical pH region extrapolated to zero buffer concentration (FIG. 2B) was also measured The pH vs. rate profile implicated the species (Bruice et al., *Bioorganic Chemistry*; Benjamin; New York, 1965; Vol. 1) involved in cleavage to be water in the pH region of 6.0 to 6.5 ($k_. = 0.6\times10^{-9}$ min$^{-1}$) and hydroxide from pH 6.6 and above ($k_{OH^-} = 4.2\times10^{-2}$ min$^{-1}$).

The ratio of $k_{cat}/k_o$, a comparison of the pH independent antibody-catalyzed hydrolysis rate of substrate Compound 3 to that hydrolysis in water, corresponds to a rate acceleration by the antibody of over a million fold. Significantly, the pH optimum of the antibody-catalyzed reaction has been moved into the neutral pH region by participation by as yet an unidentified amino acid residue, that is presumably negatively charged.

Hapten Compounds 5a and 6 were synthesized starting with 4-nitrophenethyl bromide as discussed hereinafter. The dimethyl anilinium antigen Compound 7 was prepared starting with 4-amino benzyl alcohol as is also discussed hereinafter. Conjugate of Compounds 5a, 6, and 7 produced 18, 22 and 26 hybridomas respectively, all of those monoclonal receptor molecules were of the IgG class.

Antibodies at a concentration of 20μM were initially screened (phosphate buffer, 50 mM, pH 7.5, 100 mM NaCl, 37° degrees C.) via an HPLC assay against benzoate ester Compound 3, (500 μM) for the production of 5-[(4-hydroxyphenyl)amino]-5-oxopentanoic acid, Compound 4. From the 18 monoclonals obtained to Compound 5a, three were found to be catalytic. The 22 and 26 antibodies obtained from immunizations with hapten Compounds 6 and 7, respectively, showed a negligible or an inhibitory effect on the spontaneous rate of hydrolysis of Compound 3. The three antibodies found to be catalytic were completely inhibited by the presence of 50 μM of carboxylate Compound 5b (Example 11).

The kinetics of the most efficient catalytic antibody, the monoclonal receptor secreted by hybridoma 27A6 obtained from immunizations with hapten Compound 5a was characterized in detail. That monoclonal receptor is also referred to as receptor or antibody 27A6. The initial rate of hydrolysis of Compound 3 [50 mM 4-(2-hydroxyethyl)-1-piperazinepropane sulfonic acid (EPPS), 100 mM NaCl, pH 8.5, 37° degrees C.] catalyzed by receptor 27A6 followed Michaelis-Menten kinetics with values of $K_{cat}^{app}$ and $K_m$ of 0.01±0.002 min$^{-1}$ and (243±15)X10$^{-6}$ M, respectively. The antibody-catalyzed hydrolysis of benzoate Compound 3 was competitively inhibited (K=6±2 μM) by the addition of carboxylate Compound 5b.

The pH dependence of the hydrolysis of Compound 3 was examined in the presence of monoclonal receptor 27A6 (20 μM) between pH 7.2-8.4 (EPPS) and pH values 8.4 and 10.0 [2-(cyclohexylamino)ethanesulfonic acid (CHES)], both 50 mM buffer and 100 μM NaCl, at 37° degrees C. (FIG. 3). The pH dependence of log $K_{cat}^{app}$ (FIG. 3A) was linear in this region, as were the background rate of hydrolysis (log $K_{obsd}$; FIG. 3B, closed triangles) and the rate of hydrolysis for Compound 3 extrapolated to zero buffer concentration ($K_{OH^-} = 2.3 \times 10^{-2}$ min$^{-1}$) (FIG. 3B, closed squares). The variation of the buffer concentration (12.5–50 mM) in the presence of monoclonal receptor 27A6 indicated no dependence of $K_{cat}^{app}$ on the concentration of buffer species. There was no difference in the observed rates with monoclonal receptor 27A6 when assayed at pH 8.6 in EPPS and CHES (50 mM buffer, 100 mM NaCl).

The esterolytic activity of monoclonal receptor 27A6 was unaffected by treatment with diethyl pyrocarbonate or maleic anhydride in fifty-fold molar excess to protein. Similar treatment with phenylglyoxal resulted in 75 percent loss of catalytic activity. This same antibody preparation also showed a four-fold drop in titer (binding to hapten Compound 5b (Example 11) as observed by ELISA. Identical treatment of the protein in the presence of inhibitor Compound 5b Example (11 five-fold molar excess to protein) resulted in only 35 percent loss of catalytic activity and no appreciable change in titer.

Because of these findings, other catalytic and non-catalytic antibodies to hapten Compounds 5a, 6 and 7 were chemically modified with phenylglyoxal in exactly the same manner as described above. Antibodies to Compounds 6 (2G4, 4E3, 6H4, 6A11) and 7 (52D11, 57G12, 70F3, 5G3, 60A4 were unaffected (ELISA). In contrast, five antibodies induced using Compound 5a (57G11, 60A4, 52D11 and 5G3) all showed some loss of binding (ELISA). The catalytic antibodies 57G11 ) and 70F3 showed a four-fold decrease in titer and the antibodies 60A4, 52D11, and 5G3 displayed a three-, two- and one-fold drop in titer respectively.

The before-discussed strategy based on the utilization of antibodies that were induced from a homologus series of haptens (FIG. 1) each of which possessed a point charge in close proximity to, or in direct substitution for, the chemical group (ester or amide) to be transformed in the respective substrate (FIG. 1) has been shown to be effective. It was thought that antibodies raised to these haptens should posses aming acid residue(s) at the antibody combining or binding site having a charge complementary to this haptenic charge. The substrate ester Compound 3 lacks this charge, but retains an overall similar structure. Hence, upon binding Compound 3 the aming acid residue(s) at the binding site is free from its original charge stabilization role and can now serve as a potential general acid/base or a transition-state stabilizing element.

Although antibody-hapten charge complementarity was deemed essential for the overall success of the project, two other areas of hapten design were thought to be important. The first was replacement of the acyl functionality to be hydrolyzed whereas the second necessitated the use of uncharged haptens.

The first point was addressed by using a suitable acyl moiety isostere. A hydroxylic group having a tetrahedral geometry that served as an adequate representation of the developing transition state was employed. This position was intentionally left uncharged so that there would be no additional electrostatic effects. However, it is foreseeable that "second generation haptens" might include a charged phosphorus group at this position as is disclosed in U.S. Pat. No. 4,629,567 and published European Application No. 0 260 439A2. The uncharged haptens [i.e., Compounds 2 and 6 (FIG. 1)] were needed as controls to insure the validity of the hypothesis, since they are virtually structurally identical to Compounds 1 and 5 but without a charge.

The results above showed the "bait and switch" strategy catalyzing acyl-transfer reactions to be useful when the N-methylpyridinium salt Compound 1a was employed for antibody induction. With this hapten, 30 percent of the monoclonal antibodies obtained were catalytic. Although this number was impressive, more interesting was the finding that one of these receptors employed the participation of a basic form of an ionizable group ($pK_a = 6.26 \pm 0.05$) in the catalytic process. In addition, the pH optimum of the antibody-5 catalyzed reaction was near neutrality and the utilization of neutral hapten Compound 2 showed no propensity to induce catalytic antibodies.

The hapten Compound 7 was prepared as discussed hereinafter. The most notable feature of this molecule is the tetrahedral cationic charge which directly replaces the acyl carbon of the substrate. Although this hapten might be considered even more of a radical departure from the typical phosphonate hapten surrogates of the art, it should address a number of previously unanswered questions concerning the "bait and switch" strategy. Two of concern are the importance of the cationic charge, including its placement relative to the scissile bond of the substrate and the relevance of the present acyl carbon replacement with the hydroxy isostere.

From the twenty-six antibodies raised to hapten Compound 7, none were found to accelerate the rate of hydrolysis to any appreciable extent over the background rate. This result was quite intriguing in view of the fact that a similar antigen designed by the Schultz research group showed a high propensity (66 percent) to induce catalytic antibodies for an elimination reaction [Shokat et al., *Nature (London)*, 338:269 (1989)]. Although the reactions here are quite different, the Schultz group found compelling evidence that a carboxylate was involved in the catalytic process as was found using the methylpyridinium hapten Compound 1 to induce antibodies for the esterolytic reaction. These results tied in with the findings for antibodies obtained to hapten Compounds 1a and 2 suggest the following: (1) The rate enhancements seen with monoclonal receptors induced from hapten Compound 1a are not solely due to the presence of a carboxylate acting as a catalytic base. (2) The functionality in the hapten that is used to represent the transition state is critical. (3) The combination of a cationic charge and at least a neutral representation of the transition state are required to induce hydrolytic receptor molecules.

An overall process similar to that achieved using cationic hapten Compound 1a was conceived using a structurally similar anionic hapten. The benzoic acid hapten Compound 5a filled the necessary requirements. The backbone of Compound 5a was homologous to hapten Compounds 1a and 2, while possessing an anionic point charge in close proximity to the acyl moiety we planned to hydrolyze. The choice of a carboxylate group was based on findings by Pressman that indicated that this type of functionality within a haptenic molecule has a strong propensity to induce a positively charged aming acid (i.e., lysine or arginine) within the antibody binding pocket [(a) Pressman et al., *J. Am. Chem. Soc.*, 68:250 (1946); (b) Pressman et al., *J. Am. Chem. Soc.*, 75:686 (1953); (c) Grossberg et al., *J. Am.*

*Chem. Soc.*, 82:5470 (1960)]. It was felt either aming acid residue side chain could assist in the catalytic process via general acid or electrostatic stabilization of a transition state. The latter process involving arginine residues has been implicated in enzyme catalysis [(a) Riordan et al., *Science.* (Washington, D.C.) 195:884 1977); (b) Cotton et al., *Proc. Natl. Acad. Sci. USA.* 76:2551 (1979); (c) Springs et al., *Tet. Lett.*. 32:3223 (1977).

The hydroxyethyl benzoic acid Compound 5b was synthesized. The compound was equipped with N-hydroxysuccinimide ester as Compound 5a for ease of coupling to the protein carrier. Immunizations to the Compound 5a-KLH conjugate produced eighteen monoclonal antibodies, three of which were catalytic, and whose catalysis was inhibited by free hapten Compound 5b. Although the number of catalytic receptors induced by Compound 5a was not as great as with Compound 1a, it was pleasing to find that none of the twenty-two monoclonal antibodies induced by the neutral homologue (Compound 6) of Compounds 1a and 5a was catalytic. Once again, the importance of the charged functionality contained within the antigen design is seen.

Observations on the pH-rate profile of monoclonal receptor 30C6 (induced from Compound 1a) indicated the basic form of a dissociable group was involved in catalysis. Also noted was the independence of $K_{cat}^{app}$ on the concentration of the buffer species as found with monoclonal receptor 27A6, which was induced by Compound 5a (FIG. 1). In contrast to the behavior of receptor 30C6, came the findings of a pH dependence of $K_{cat}^{app}$ with receptor 27A6 (FIG. 3A). Although this finding appears to contradict the essence of the "bait and switch" theory, it is thought that the $pK_a$ of the combining site aming acid residue side chain(s) may lie outside the pH range investigated, or that protein-substrate electrostatic interactions (electrostatic catalysis) is the essential feature of this receptor's ability to accelerate the reaction [Fersht, *Enzyme Structure and Mechanism*, Freeman, eds., New York (1985)].

Although unable to detect any aming acid involvement in receptor 27A6 hydrolytic reaction via pH effects, a specific inactivation of all three (27A6, 57G12, 70F3) catalytic antibodies was observed through the use of the arginine modifying reagent phenylglyoxal [Takahashi, *J. Biol. Chem.*, 243:6171 (1968)]. The loss of activity (catalytic/binding) can be interpreted as due to reaction of the reagent with an amino acid residue side chain in the binding site; it can be reduced significantly by the presence of hapten Compound 5b (Example 11).

However, a conformation change following reaction of the reagent at a different site would lead to a similar conclusion. Thus, it is possible that an arginine residue somewhere other than in the binding site is chemically altered leading to stabilization of conformations of the protein in which the binding site is altered so that it no longer binds substrate Compound 3 or hapten Compound 5b (Example 1D). This complication does not appear to apply here.

Catalytic and ELISA assays demonstrate and previous binding studies noted by Freedman et al., *Immunochem.*, 9:169 (1972) and Mayers et al., *Immunochem.*, 9:169 (1972), that glyoxalation of guanidinium groups destroys catalytic and/or binding activity only of antibodies against negatively charged haptens, and not of antibodies against neutral hapten Compound 6 or positively charged hapten Compound 7. If glyoxalation exerted an effect by altering a guanidinium distant from the binding site by the above mechanism, it is difficult to see why antibodies to the Compound 6 or 7 haptens would not be similarly affected. It is thus believed that an arginine, whose guanidium side group has a $pK_a$ value above the range studied here, is in the binding site and is involved with the observed catalysis.

An ensemble of multiple charges that can produce a number of catalytic groups is foreseen, giving an additive rate effect. This effect combined with access to a much larger repertoire of potential catalytic antibodies [Shastry et al., *Proc. Natl. Acad. Sci. USA.* 86:5728 (1989)] improves the probability of developing superior catalysts.

V. Ligand Preparation

Unless otherwise noted, reactions were carried out in flame-dried glassware under an atmosphere of nitrogen. Reagent and solvent transfers were made with oven-dried syringes and needles. Dichloromethane and acetonitrile were continuously distilled from calcium hydride. Tetrahydrofuran a (THF) was distilled from sodium metal/benzophenone ketyl. All reagents were purchased from Aldrich Chemical Company. All chromatography solvents were obtained commercially and used as received. Reactions were monitored by analytical thin-layer chromatographic methods (TLC) with the use of E. Merck silica gel 60F glass plates (0.25 mm). Flash chromatography was carried out with the use of E. Merck silica gel 60 (230-400 mesh) as described by Still et al., *J. Org. Chem.*, 43:2923 (1978).

Melting points were determined on a Fisher-Johns melting point apparatus and are uncorrected. All proton NMR spectra (300 MHz) were obtained in CDCl$_3$, CD$_3$CN, or DMSO solutions at ambient temperature on a Bruker AM-300 spectrometer, chemical shifts ($\alpha$) are reported in parts per million relative to internal tetramethylsilane (0.00 ppm). Elemental analyses (C, H, N) were performed by Galbraith Laboratories, Knoxville, Tenn.

EXAMPLE 1 p-Nitrophenylacetaldehyde p-Nitrophenylacetaldehyde was prepared by the method described in Lethbridge et al., *J. Chem. Soc. Perkin I*, 35 1973) from p-nitrophenylethylene. The p-nitrophenylethylene was prepared by the method described in Strassburg et al., *J. Am. Chem. Soc.* 69:2142 (1947) from 1-bromo-2-(p-nitrophenyl)ethane commercially obtainable from Aldrich Chemical Co., Milwaukee, Wis.).

EXAMPLE 2

Compound I n-Butyl-lithium (3.33×10$^{-2}$ moles) was added to tetrahydrofuran (THF; 100 ml) maintained at $-100°$ degrees C. in an ether/nitrogen bath. 2-Bromo-pyridine (3.64×10$^{-2}$ moles) was added to this mixture with stirring for 15 minutes. The reaction mixture was raised to $-78°$ degrees C. by transferring the reaction vessel to an acetone/CO$_2$ bath, and the mixture was stirred for 1 hour.

p-Nitrophenylacetaldehyde (5 grams, 3.03×10$^{-2}$ moles), obtained from Example 1, dissolved in THF (30 ml), was slowly added to the reaction mixture, and the mixture was stirred for 3 hours at $-78°$ degrees C.

Following stirring, the mixture was poured into a saturated solution of ammonium chloride (500 ml) and diethyl ether. The mixture was extracted two times with diethyl ether, the combined ether layers were dried over sodium sulfate, and run on a column in 15 percent CH$_3$CN in CH$_2$Cl$_2$. The product, Compound I (1-hydroxy-1-(2-pyridinyl)-2-(p-nitrophenyl) ethane), was collected to yield 648 mg (2.7×10$^{-3}$ moles, 9 percent yield). $^1$H NMR δ8.55 (d, 1H): 8.10 (d, 2H): 7.65 (m, 1H): 7.3 (d, 2H): 7.2 (m, 2H): 5.05 (dd, 1H): 3.20 (m, 2H).

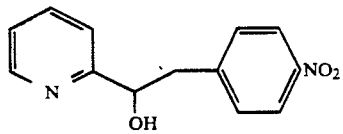

Compound I

EXAMPLE 3

Compound II

Dry methanol (12 ml) was added to a dry 25 ml reaction vessel, flushed with nitrogen.

Compound I (100 mg), obtained in Example 2, was dissolved into the methanol to produce an orange-colored solution. The solution was flushed with nitrogen and 10 percent palladium on carbon (Pd/C, 75 mg) was added to the solution. The sides of the reaction vessel were washed with a small amount of methanol and the solution was flushed with nitrogen and then flushed with hydrogen. The reaction mixture was stirred for about 1 hour, and then filtered through a bed of Celite. The filter was rinsed 4 times with dichloromethane (CH$_2$Cl$_2$), and then rinsed 3 times with methanol until no thin-layer chromatographic (TLC) spotting material was obtained from the filter. The filtrate rinses were dried with sodium sulfate and evaporated to dryness to yield 85.6 mg (97.6 percent yield) of yellow crystalline solid, Compound II (1-hydroxy-1-(2-pyridinyl)-2-(p-aminophenyl)ethane).

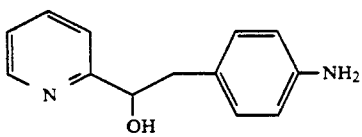

Compound II

EXAMPLE 4

Compound 2

Compound II (155 mg, 7.24×10$^{-4}$ moles), from Example 3, was mixed with dry CH$_2$Cl$_2$ (1.5 ml) and triethylamine [(Et$_3$N)(1.45×10$^{-3}$ moles)]. N-hydroxysuccinimidoyl glutaroyl chloride (359 mg, 1.45×10$^{-3}$ moles) was added and the resulting reaction mixture was stirred at 25° degrees C. for about 40 minutes. The reaction product was evaporated to dryness by rotoevaporation, yielding 61.5 mg 20 percent yield) of 5-[(2,5-dioxo)-1-pyrolidinyl)oxy]-N-[4-[2-hydroxy-2-(2-pyridinyl)ethyl]phenyl]-5(Compound 2).

$^1$H NMR (DMSO-d$_6$) δ9.82 (s 1H); 8.48 (d 1H J=4.3 Hz); 7.75 (dd, 1H, J=2×7.6 Hz); 7.42 (d, 2H, J=7.9 Hz); 7.22 (m, 2H); 7.05 (d, 2H, J=7.9 Hz); 5.38 (d, 1H, J=5.1 Hz); 4.76 (dd, 1H, J=4.0,3.5 Hz); 3.05 (dd, 2H, J=13.7, 4.0 Hz); 2.80 (s, 4H); 2.76 t, 2H, J=8.2 Hz); 2.42 (t, 2H, J=8.2 Hz); 1.90 (m, 2H).

Anal. Calcd. for C$_{22}$H$_{23}$N$_3$O$_6$: C, 62.12; H, 5.41; N, 9.88. Found: C, 62.19; H, 5.37; N, 9.92 percent.

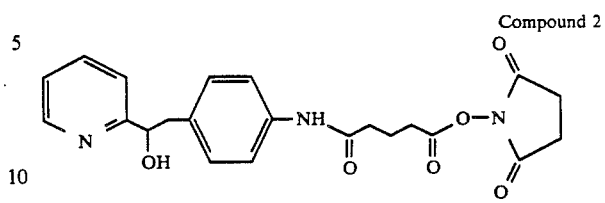

Compound 2

EXAMPLE 5

Compound 1a

Compound 2 (30 mg, 7.06×10$^{-5}$ moles), from Example 4, was mixed with methyl iodide (7.06×10$^{-4}$ moles) in acetone (0.5 ml) and refluxed for about 17 hours. The reaction mixture was rinsed 3 times with chloroform and then rinsed 3 times with hot ethyl acetate to yield 20 mg 50 percent yield) of haptenic ligand 2-[2-[5-[(2,5-dioxo-1-pyrolidinyl)oxy]-1,5-dioxopentyl]-4-aminophenyl]-1-hydroxyethyl]-1-methyl-pyridinium iodide, (Compound 1a).

$^1$H NMR (DMSO-d$_6$) δ9.86 (s, 1H); 8.92 (d, 1H, J=6.1 Hz); 8.55 (d, 1H, J=8.0 Hz); 8.08 (t, 1H, J=6.8 Hz); 8.00 (t, 1H, J=7.9 Hz); 7.48 (d, 2H, J=7.9 Hz); 7.12 (d, 2H, J=7.9 Hz); 6.30 (d, 1H, J=5.1 Hz); 5.34 (dd, 1H, J=4.0, 3.5 Hz); 4.35 (s, 3H); 3.02 (dd, 2H, J=13.6, 4.0 Hz); 80 s, 4H); 2.72 (t, 2H, J=8.2 Hz); 2.45 (t, 2H, J=8.2 Hz); 1 90 (m, 2H).

Anal. Calcd. for C$_{23}$H$_{26}$N$_3$O$_6$I: C, 48.67; H, 4.59; N, 7.41. Found: C, 48.11; H, 4.51; N, 7.37 percent.

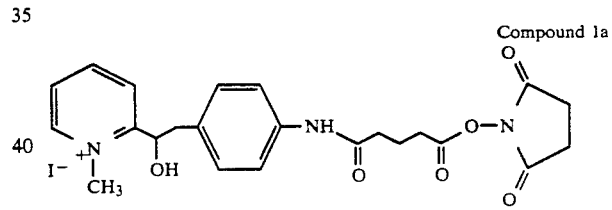

Compound 1a

EXAMPLE 6

2-[(4-Nitrophenyl)methyl]-1,3-Dioxolane (Compound III)

p-Nitrophenylacetaldehyde (500 mg, 3.0×10$^{-3}$ moles) was dissolved in CH$_2$Cl (about 1.5 ml). CaSO$_4$ (383 mg) was added to the mixture followed by Rexyn 101 resin (proton form, Fisher Scientific; 128 mg) and ethylene glycol (13.8×10$^{-3}$ moles). The mixture was stirred under nitrogen for about 4 hours. Prior to use, the Rexyn 101 and CaSO$_4$ were maintained for 20 hours at about 120° degrees C. in a drying oven and then cooled in a desiccator.

A sample was removed and spotted on a TLC in neat CH$_2$Cl$_2$. Additional Rexyn 101 and CaSO$_4$ were added, and the mixture was stirred overnight (about 16-18 hours). CH$_2$Cl$_2$ (10 ml) was added to the stirring mixture. A sample was spotted on TLC and showed no spotting material.

Water (10 ml) was added, the mixture was stirred and the organic layer was separated, dried with sodium sulfate, and purified by flash chromatography using hexane:ethylacetate (2:1) to yield 435.8 mg (70 percent yield) of Compound III.

¹H NMR: δ8.10 (d, 2H); 7.4 (d, 2H); 5.10 (t, 1H); 3.8 (s, 4H); 3.0 (d, 2H).

In a second preparation, ethylene glycol (5.4 ml, 97 mmol) was added to a stirred solution of p-nitrophenylacetaldehyde (3.0 g, 18.2 mmol) in 10.0 ml methylene chloride. To this was added 1.0 g Rexyn 101 (H) (Fisher Scientific) cation exchange resin and 3.0 g powdered calcium sulfate, that had been oven dried (120° degrees C.) overnight. The mixture was stirred for 24 hours at room temperature, and the reaction mixture was subsequently poured into 100 ml H$_2$O, and extracted three times with 50 ml portions of methylene chloride. Combined organic layers were dried with sodium sulfate and purified by flash chromatography, 2:1 hexanes:ethyl acetate yielding 2.28 g, 60 percent of the theoretical amount.

¹H NMR (CDCl$_3$) δ8.18 (d, J=8.6 Hz, 2H), 7.42 (d, J=8.6 Hz, 2H), 5.08 t, J=4.3 Hz, 1H), 3.8-4.0 (m, 4H), 3.06 (d, J=4.3 Hz, 2H).

Anal. Calcd. for C$_{10}$H$_{11}$NO$_4$: C, 57.42; H, 5.26; N, 6.70. Found: C, 57.51; H, 5.19; N, 6.65.

EXAMPLE 7

4-(1,3-Dioxolan-2-ylmethyl)-benzenamine (Compound IV)

Compound III (231 mg), from Example 6, was dissolved in methanol (about 3 ml) and the mixture flushed with nitrogen. Pd/C (120 mg) was added to the mixture and the sides of the reaction flask were rinsed with methanol (about 2 ml). The mixture was flushed with nitrogen and then flushed with hydrogen. The reaction mixture was stirred for 45 minutes, and then filtered through Celite. The Celite was rinsed several times with methanol and the filtrate and rinses were rotoevaporated to yield 184.4 mg (90.6 percent yield) of Compound IV.

In another preparation, Compound III (2.0 g, 9.6 mmol) was added to 20 ml methanol. To this suspension 10 percent palladium on activated carbon (200 mg) was added, and the flask was fitted with a balloon of hydrogen and stirred rapidly at room temperature for six hours. The reaction mixture was filtered through celite and concentrated yielding 1.63 g, 95 percent of the theoretical amount. This material was utilized without further purification in the repeat of the following example. TLC R$_f$=0.3, 1:1 ethyl acetate:hexanes.

EXAMPLE 8

N-[4-(1,3-Dioxolan-2-ylmethyl)phenyl-N-phenylmethyl)-benzenemethanamine (Compound V)

Compound IV (1.91 gm, 1.07×10$^{-2}$ moles), from Example 7, was mixed with CH$_2$Cl$_2$ (10 ml) and Et$_3$N (4.45 ml, 3.2×10$^{-2}$ moles), and stirred. Benzylbromide (1.07×10$^{-1}$ moles) was added dropwise to the stirred mixture, after about half of Compound IV was dissolved in the solution. All of the amine then dissolved. The reaction was stopped after about one hour. The solution was run on a column in CH$_2$Cl$_2$:HCl (9:1) and 3.048 mg (79 percent yield) of the desired product was collected (Compound V):

¹H NMR: δ7.25 (s, 10H); 7.05 d, 2H); 6.85 (d, 2H); 5.00 (t, 1H); 4.60 (s, 4H); 3.9 (m, 4H); 2.8 (d, 2H).

Repeating the above synthesis, to a stirred suspension of Compound IV (2 g, 11.2 mmol) in 10 ml of methylene chloride was added triethylamine (4.5 ml, 32 mmol). Addition of benzyl bromide (6.4 ml, 107 mmol) was done dropwise over 30 minutes with rapid stirring, with the resulting mixture being stirred for an extra 60 minutes. The reaction mixture was diluted with methylene chloride (50 ml) and extracted with (2×25 ml) 0.5 M HCl. The combined organic extracts were dried with sodium sulfate and purified by flash chromatography in 4:1 methylene chloride:hexanes, yielding 3.2 g, 80 percent of the theoretical amount. H NMR (CDCl$_3$) δ 7.35-7.23 (m, 10H), 7.06 (d, J=8.6 Hz, 2H) 6.66 (d, J=8.6 Hz, 2H) 5.50 (5, J=4.3 Hz, 1H), 4.62 (s, 4H), 3.8-4.00 (m, 4H), 2.82 (d, J=4.3 Hz, 2H). Anal. Calcd. for C$_{24}$H$_{25}$NO$_2$: C, 80.22; N, 6.96; N, 3.90. Found: C, 80.35; H, 7.11; N, 3.86.

EXAMPLE 9

4-[Bis(phenylmethyl)amino-benzeneacetaldehyde (Compound VI)

Compound V (2 g, 5.6×10$^{-3}$ moles), from Example 8, was dissolved in acetone (6 ml) and stirred under nitrogen. 4M HCl (6 ml) was added to the mixture and stirring continued until the reaction mixture was slightly yellow. The reaction mixture was transferred to a separation funnel containing CH$_2$Cl$_2$ and washed with aqueous NaCl. The organic layer was dried with sodium sulfate and stored under vacuum overnight (16-18 hours).

A sample was run on TLC and staining with ninhydrin showed 5 spots in CH$_2$Cl$_2$:hexane (4:1). The reaction product was placed on a 50 mm preabsorbed silica column and 500 mg (29 percent yield) of the spot corresponding to the desired product (Compound VI) was collected.

¹H NMR: δ9.5 (t, 1H); 7.1 (s, 10H); 6.8 (d, 2H); 4.5 (s, 4H); 3.4 (d, 2H).

In another preparation, to a solution of 2.0 g (5.6 mmol) of Compound V in 15 ml of acetone were added 2 ml of 4M HCl. This solution was stirred 24 hours at room temperature. Silica (lo g) was added to the reaction mixture, and the mixture was concentrated to dryness. Flash chromatography was run in 4:1 methylene chloride:hexanes with the pre-absorbed crude reaction product, yielding 0.7 g, 40 percent of the theoretical amount. ¹H NMR (CDCl$_3$) δ 9.7 (t, J=2.9 Hz, 1H), 7.40-720 (m, 10H), 7.00 (d, J=8.6 Hz, 2H), 6.7 (d, J=8.6 Hz, 2H), 4.66 (s, 4H), 3.54 (d, J=2.9 Hz, 2H). Anal. Calcd. C$_{22}$H$_{21}$NO: C, 83.81; H, 6.67; N, 4.44. Found: C, 84.06; H, 6.58; N, 4.50.

EXAMPLE 10

2-[2-(4-Aminophenyl-1-hydroxyethyl]-benzoic acid (Compound VII)

2-Bromobenzoic acid (88 mg, 4.33 ×10$^{-4}$ moles) was dissolved in THF (2 ml) and cooled to −78° degrees C. n-Butyl lithium (n-buLi) (8.38×10$^{-4}$ moles) was added, and the mixture stirred for two hours.

Compound VI (91 mg, 2.89×10$^{-4}$ moles), obtained in Example 9, dissolved in THF (1 ml) was added to the mixture and the mixture was stirred for four hours at −78° degrees C. The reaction mixture was diluted into ethyl acetate and washed two times with saturated NH$_4$Cl, followed by one washing with 1M HCl. The organic fraction was separated, dried with sodium sulfate, and rotoevaporated overnight (about 16-18 hours).

TLC of the product in CH$_2$Cl$_2$:hexane (4:1) showed two spots. Both spots were collected from a column. The desired product was obtained to provide 32 mg (25 percent yield) as Compound VII. ¹H NMR: 7.1-7.8 (m, 14H); 6.9 (d, 2H); 6.6 (d, 2H); 5.6 (t, 1H); 4.6 (s, 4H); 3.0 (m, 2H)

In another preparation, 2-bromobenzoic acid (957 mg, 4.8 mmol) was dissolved in 20 ml of tetrahydrofuran and cooled to −78° degrees C. (CO₂/acetone), n-butyl lithium (n-BuLi; 5.8 mM, 1.6M in hexanes, 9.2 mmol) was added nd stirred for one hour. Aldehyde Compound VI, (1.9 g, 3.2 mmol) dissolved in 10 ml tetrahydrofuran cooled to −78° degrees C. was added Via cannula, and thereafter stirred for four hours at −78° degrees C. The reaction mixture was poured into saturated ammonium chloride followed by extraction with (2×50 ml) ethyl acetate. The combined organic extracts were dried with sodium sulfate and purified by flash chromatography using neat methylene chloride yielding 860 mg, 62 percent of the theoretical amount. ¹H NMR CDCl₃) δ7.90–7.80 (m, 1H), 7.68–7.40 (m, 2H), 7.40–7.05 (m, 11H), 7.0 (d, J=8.6 Hz, 2H), 6.64 (d, J=8.6 Hz, 2H), 5.62 (t, J=7.1 Hz, 2H), 3.64 (br s, 2H), 3.4–2.8 (m, 2H).

Anal. Calcd. C₂₉H₂₇NO₃: C, 80.37; H, 6.24; N, 3.23. Found: C, 80.44; H, 6.29; N, 3.19.

EXAMPLE 11

2-[2-[4-[Bis(phenylmethyl)amino]phenyl]-1-hydroxyethyl]-benzoic acid (Compound 5b)

Compound VII (32 mg), obtained in Example 10, was dissolved in methanol (2 ml). Pd/C (10 mg) was added and the reaction mixture flushed with hydrogen and stirred for about 1.5 hours until all spotting material was gone, as determined by TLC in CH₂Cl₂:ethylacetate (1:1), yielding 16.2 mg (86 percent yield) of Compound 5b.

In a repeat synthesis, carboxylate Compound VII (320 mg, 7.3×10⁻⁴ mols) was dissolved in 20 ml of methanol. This was followed by the addition of 10 percent palladium on activated carbon (32 mg), charging of the flask with hydrogen, and rapid stirring for 90 minutes. Filtration through celite followed by concentration yielded 179 mg, 95 percent of the theoretical amount. This material was employed without further purification in the repeat of the following example. TLC R$_F$=0.6, 1:1 methylene chloride:ethyl acetate.

EXAMPLE 12

2-[2-[4-[[5-[(2,5-Dioxo-1-pyrolidinyl)oxy]-phenyl]-1-hydroxyethyl -benzoic acid (Compound 5a)

Compound 5b (16.2 mg, 6.3×10⁻⁵ moles), obtained in Example 11, was dissolved in CH₂Cl₂ (70 µl), and Et₃N (1.26×10⁻⁴ moles) was added with stirring.

N-hydroxysuccinimidoyl glutaroyl chloride (19.1 mg, 8.19×10⁻⁵ moles) was added, and the reaction mixture was stirred under nitrogen. The reaction mixture was then put directly onto a preparative TLC plate and eluted with CH₂Cl₂:ethylacetate (1:1) to provide 14.3 mg (50 percent yield) of the desired haptenic ligand Compound 5a.

¹H NMR: δ9.2 (s, 1H); 7.2–6.8 (m, 6H); 6.6 (d, 2H); 5.2 (t, 1H); 2.6 (m, 2H); 2.1 (s, 4H); 2.0 (t, 2H); 1.8 (t, 2H); 1.4 (m, 2H).

In a repeat synthesis, carboxylate VIII (100 mg, 3.9×10⁻⁴ mol) was dissolved in 800 µl of methylene chloride and triethylamine (109 µl, 7.8×10<mol). That dissolution was followed by addition of (5-[(2,5-dioxo-1-pyrolidinyl)oxy]-5-oxo-pentanoyl chloride (118 mg, 5.1×10 mol) and stirring for 20 minutes. Purification was performed by loading the crude reaction mixture onto a flash chromatography column and eluting with 1:1 methylene chloride:ethyl acetate yielding 159 mg, 90 percent of the theoretical amount.

¹H NMR (CDCl₃) δ9.24 (s, 1H), 7.36–6.8 (m, 6H), 6.42 d, J=8.6 Hz, 2H) 5.20 t, J=7.1 Hz, 1H), 2.66–2.36 (m, 2H), 2.15 (S, 4H), 2.1–1.96 (m, 2H), 1.96–1.7 (m, 2H), 1.5–1.16 (m, 2H).

Anal. Calcd. C₂₄H₂₄N₂O₈: C, 61.54; H, 5.13; N, 5.98. Found: C, 61.62; H, 5.10; N, 5.89.

EXAMPLE 13

Compound II

Compound II, from Example 3 (262 mg, 1.22×10⁻³ moles), and glutaric anhydride (140 µg) were dissolved in CH₂Cl₂ (10 ml) and stirred for 16 to 18 hours. More glutaric anhydride (40 µg) was added to the solution and the reaction mixture was stirred for 3 hours and then poured into an aqueous solution of Et₃N 1.47×10⁻moles). The solution was then diluted with ethyl acetate, and the aqueous layer removed and acidified with trifluoroacetic acid (TFA). The aqueous layer was extracted with ethyl acetate, purified by HPLC using a standard 10:90 to 90:10 CH₂CN:H₂O gradient, and 240 mg (60 percent yield) of the desired compound (Compound IX) was obtained.

¹δ8.3 (m, 3H); 7.6 (t, 2H); 6.9 (d, 2H); 6.7 (d, 2H); 5.1 (t, 1H); 2.8 (m, 2H); 2.0 (m, 4H); 1.5 (m, 2H).

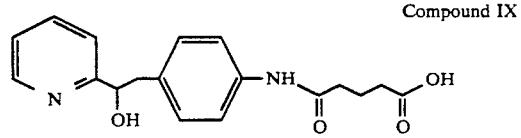

Compound IX

EXAMPLE 14

Compound 1b

Compound IX (58 mg, 1.77×10⁻⁴ moles), from Example 13, was mixed with methyl iodide (8.84×10⁻⁴ moles) and dissolved in a sealed tube in acetone (about 5 ml), and heated for about 16 to 18 hours at 80° degrees C. The precipitate was filtered and rinsed with CHCl₃ to yield 56 mg (67 percent yield) of Compound 1b.

¹H NMR: δ8.5–7.5 (m, 4H); 7.2–6.8 (m, 4H); 5.2 (t, 1H); 3.2 (m, 2H); 2.2 (t, 2H); 1.8 (t, 2H); 1.2 (m, 2H).

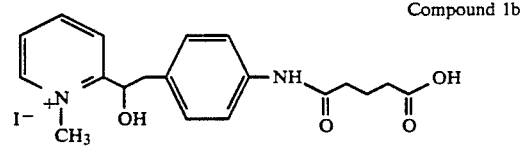

Compound 1b

EXAMPLE 15

Compound X p-Nitrophenol (1 gm, 7.19×10⁻³ moles) was dissolved in CH₂Cl₂ (3 µl) and Et₃N (7.19×10⁻³ moles) was added to produce a yellow-colored solution.

Benzylchloride (8.63×10⁻³ moles) was added dropwise to the solution, resulting in some boiling. The yellow color dissipated after about 5 minutes and a precipitate formed. CH₂Cl₂ (2 ml) was added to the precipitate-containing solution, followed by the addition of ethyl acetate (3 ml) which dissolved the precipitate. The solution was stirred for one hour.

The solution was mixed with water and stirred for about 45 minutes, followed by a washing in 1M HCl, and then two washes with 10 percent NaHCO3, two washes with 1M HCl, and two washes with saturated NaCl. The organic layer was dried with sodium sulfate, rotoevaporated, stored under vacuum, and separated on a column in CH2Cl2:hexane (2:1 . The lower R$_f$ spot on TLC was collected, yielding 1 2613 g (72 percent yield) of Compound X (p-nitro-phenylbenzoate).

$^1$H NMR: δ8.4–8.0 (m, 4H); 7.7–7.3 (m, 5H)

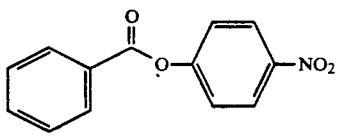

Compound X

EXAMPLE 16

Compound XI

Compound X (530 mg, $2.18 \times 10^{-3}$ moles), from Example 15, 12M HCl (200 μl), Pd/C (275 mg) and hydrogen gas were mixed in methanol (about 15 ml ) and stirred for 2.5 hours under nitrogen until all spotting material, as determined by TLC in CH2Cl2:MeOH (9:1), was gone. The solution was filtered and dried to yield 518 mg (95 percent yield) of Compound XI.

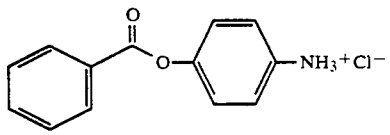

Compound XI

EXAMPLE 17

Compound 3

Compound XI (518 mg, $2.08 \times 10^{-3}$ moles), from Example 16, was mixed with CH2Cl2 (10 ml) and glutaric anhydride (260 μg, $2.28 \times 10^{-3}$ moles). Et3N ($4.58 \times 10^{-3}$ moles) was dissolved into the solution and the reaction mixture was stirred for 16 to 18 hours.

TLC showed spotting material in CH2Cl2:ethylacetate (9:1). More glutaric anhydride (0.25 mg) was added to the solution and the reaction mixture was stirred for an additional three hours until all spotting material was gone. The solution was diluted with ethylacetate, washed two times with 1M HCl. The organic phase dried with sodium sulfate and evaporated to yield 655 mg of crude product. The crude product was purified by FPLC in CH3CN:CH3OH:H2O (4:1:4) to yield 397 mg of Compound 3.

$^1$H MMR: δ9.9 (s, 1H); 8.1 (d, 2H); 7.7–7.4 (m, 5H); 7.1 (d, 2H); 2.3 (t, 4H); 1 8 (m, 2H).

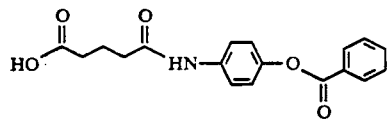

Compound 3

EXAMPLE 1

Compound 4

Glutaric anhydride (1.34 gm, $1.17 \times 10^{-2}$ moles) and p-aminophenol (1.6 gm, $1.47 \times 10^{-2}$ moles) were dissolved in CH2Cl2 (5 ml) and stirred at 35° degrees C. for one hour. The mixture was diluted into ethyl acetate, and washed two times with 1M HCl. The organic layer was dried with sodium sulfate and rotoevaporated. HPLC showed the product to be dissolved in the aqueous layer, which was lyophilized to yield 214 mg of the crude product.

The crude product was dissolved in H2O (16 ml), methanol (5 ml), and CH3CN (5 ml) and purified by FPLC to yield 89 mg of Compound 4. $^1$H NMR: δ9.6 (s, 1H); 7.3 (d, 2H); 6.6 (d, 2H); 2.2 (m, 4H); 1.7 (m, 2H).

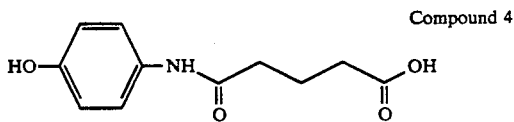

Compound 4

EXAMPLE 19

2-[2-(4-Aminophenyl)-1-hydroxyethyl]-1-methyl benzene (Compound XII)

n-BuLi (2.8 ml, 2.6 M in hexanes, 4.4 mmol) was added to 30 ml THF and cooled to −78° degrees C. (CO2/acetone). To this solution, 2-bromotoluene (0.573 ml, 4.8 mmol) was added and allowed to stir 30 minutes. Aldehyde Compound VI, (1.9 g, 3.2 mmol) dissolved in 15 ml of THF and cooled to −78° degrees C. was next added, and the resulting mixture stirred for two hours. The reaction mixture was poured into a saturated ammonium chloride solution and extracted 2×25 ml with methylene chloride. The combined organic layers were dried with sodium sulfate and purified by flash chromatography in 6:1:1.5 hexanes:methylene chloride:ethyl acetate yielding 900 mg of Compound XII, 69 percent of the theoretical amount. $^1$H NMR (CDCl3) δ7.9–7.8 (m, 1H), 7.68–7.40 (m, 2H), 7.40–7.15 (m, 12H), 7.05 (d, J=8.6 Hz, 2H), 6.70 (d, J=8.6 Hz, 2H), 5.3 (t, J=7.1 Hz, 1H), 4.62 (s, 4H) 3,0–2.7 (m, 2H), 2.3 (s, 3H). Anal. Calcd. for C29H29NO: C, 85.50; H, 7.13; N, 3.44. Found C, 85.58; H, 7.08; N, 3.41.

EXAMPLE 20

2-[2-[4-[Bis(Phenylmethyl)amino]phenyl]-1-hydroxyethyl]-1-methyl benzene (Compound XIII)

To a solution of Compound XII (900 mg, 2.2 mmol) in 50 ml of ethyl acetate was added 10 percent palladium on activated carbon (100 mg). The reaction vessel was pressurized to 50 psi with hydrogen on a PARR hydrogenation apparatus. The reaction was complete after four hours, and was then filtered through celite and concentrated in vacuo yielding 476 mg of Compound XIII, 95 percent of the theoretical amount. This material was used without further purification in the next example. TLC R$_f$=0.05, 4:1 methylene chloride:-hexanes.

EXAMPLE 21

2-[2-[4-Carboxy-1-oxobutyl)amino]phenyl]-1-hydroxyethyl]-1-methyl benzene (Compound 6)

To a solution of Compound V (476 mg, 2.1 mmol) in 10 ml of methylene chloride containing triethylamine (351 μl, 2.5 mmol) was added (5-[(2,5-dioxo-1-pyrolidinyl)oxyl]-5-oxo-pentanoyl chloride (572 mg, 2.3 mmol). The solution stirred 30 minutes upon which time it was diluted with ethyl acetate (25 ml), washed with 1M HCl (2×15 ml), and dried with sodium sulfate. The crude material was purified by flash chromatography, 1:1 methylene chloride:ethyl acetate yielding 780 mg of Compound 6, 85 percent of the theoretical amount.

¹H NMR (CDCl₃) δ9.24 (s, 1H), 7.4–6.85 (m, 6H), 6.45 (d, J=8.6 Hz, 2H), 5.20 (t, J=7.1 Hz, 1H), 2.65–2.4 (m, 2H) 2.3 (s, 3H), 2.15 (s, 4H), 2.1-1 96 (m, 2H), 1.96–1.72 (m, 2H), 1.5–1.20 (m, 2H).

Anal. Calcd. for $C_{24}H_{26}N_2O_6$: C, 65.75; H, 5.94; N, 6.39. Found: C, 65.79; H, 5.91; N, 6.41.

EXAMPLE 22

5-[(2,5-Dioxo-1-pyrolidinyl)ox]-N-[4-(hydroxymethyl)-phenyl]-5-oxo-pentanamide (Compound XIV)

To a solution of triethylamine (1.13 ml, 8.2 mmol) in 10 ml of methylene chloride, p-aminobenzyl alcohol (1.9 g, 8.1 mmol) was dissolved. To this solution, (5-[(2,5-dioxo-1-pyrolidinyl)oxy]-5-pentanoyl chloride (2.21 g, 8.9 mmol) was added and stirred for one hour. The reaction mixture was diluted with methylene chloride (25 ml) and extracted with 2×26 ml of a 2M HCl solution. The resultant organic layer was dried with sodium sulfate and purified by flash chromatography in 9:1 methylene chloride:methanol yielding 2.43 g of Compound XIV, 90 percent of the theoretical amount.

¹H NMR CDCl₃) δ 8.0 br x, 2H), 7.52 d, J=8.6 Hz, 2H), 7.30 (d, J=8.6 Hz, 2H), 4.62 (s, 2H), 3.45 (s, 2H), 2.9 s, 4H), 2.75 t, J-10 Hz, 2H), 2.5 (t, J=10 Hz, 2H), 2.38–2.10 (m, 2H).

Anal. Calcd. for $C_{16}H_{18}N_2O_6$: C, 57.49; H, 5.39; N, 8.38. Found: C, 57.42; H, 5.44; N, 8.29.

EXAMPLE 23

N-[4-(Bromomethyl)phenyl]-5-[(2,5-dioxo-1-pyrolidinyl)oxyl-5-oxo-pentanamide (Compound XV).

To a solution of Compound XIV (2.9 g, 6 mmol) in 20 ml of dimethyl formamide was added dibromotriphenylphosphorane (3.04 g, 7.2 mmol). The reaction mixture was subsequently warmed to 50° degrees C. and stirred for four hours. The reaction mixture was then diluted with one liter of ethyl acetate, extracted with brine (4×200 ml) and dried over sodium sulfate. Purification via flash chromatograph, 1:1 ethyl acetate:methylene chloride yielded 1.20 g of Compound XV, 50 percent of the theoretical amount. ¹H NMR (CDCl₃) δ 8.0 (br s, 1H), 7.50 , (d, J=8.6 Hz, 2H), 7.39 (d, J=8.6 Hz, 2H), 4.5 (s, 2H), 2.9 (s, 4H), 2.75 (t, J=10 Hz, 2H), 2.5 (t, J=20 Hz, 2H), 2.38–2.10 (m, 2H).

Anal. Calcd. for $C_{16}H_{17}N_2O_5$: C, 58.72; H, t.20; N, 8.56. Found: C, 58.66; H, 5.24; N, 8.50

EXAMPLE 24

(4-[[5-[(2,5-Dioxo-1-pyrolidinyl)oxyl]-1,5-dioxopentyl-]amino]-N,N-dimethyl-N-bromidebenzenemethanaminium-bromide (Compound 7)

Bromide Compound XV (1.9 g, 2.5 mmol) was dissolved in 60 ml of methylene chloride, followed by the addition of dimethyl aniline (1.6 ml, 12.5 mmol). The solution stirred for 30 minutes upon which time a precipitate formed; stirring continued for four hours. The formed suspension was transferred to a separating funnel and extracted with 3×30 ml distilled water. The combined aqueous washes were lyophilized to obtain 1.17 g of product Compound 7, 90 percent of the theoretical amount ¹H NMR (D₂O) δ 7.60 (s, 5H), 7.38 (d, J=8.6 Hz, 2H), 7.9 (d, J=8.6 Hz, 2H), 4.95 (s, 2H), 3.62 (s, 6H), 2.9 (s, 4H), 2.75 (t, J=10 Hz, 2H), 2.5 (t, J=10 Hz, 2H), 2.38–2.10 (m, 2H).

Anal. Calcd. for $C_{24}H_{28}N_3O_5Br$: C, 55.60; H, 5.41; N, 8.11. Found C, 55.67; H, 5.39; N, 8.07.

EXAMPLE 25

Preparation of Succinimidyl Adipoyl and Glutaroyl chlorides (Coupling Agents)

A solution of adipic acid monomethyl ester (5.4 g, 33.3 mmol) in thionyl chloride (15 ml) was heated at 40° degrees C. for two hours. The mixture was then concentrated and distilled in vacuo (boiling point 119° degrees C. at 20 mm Hg) to provide 3.58 g (60 percent yield by weight) of the acid chloride methyl ester. This was dissolved in 20 ml of dichloromethane and N-hydroxysuccinimide (2.75 g, 24.0 mmol) was added, followed by triethylamine (4.2 ml, 30 mmol). The mixture stirred for 10 minutes then diluted with ethyl acetate and washed with 0.5M HCL and brine. The solution was dried over anhydrous magnesium sulfate, filtered and concentrated to give 4.5 g (87.5 percent yield by weight) of methyl succinimidyl adipate) as a colorless oil.

Proton NMR in CDCl₃ at 100 MHz (relative to TMS as internal standard): delta 3.73 (singlet, 3H), delta 2.90 (singlet 4H), 2.70 (multiplet, 2H), 2.37 (multiplet, 2H), and 1.79 (multiplet 4H).

A solution of methyl succinimidyl adipate (4.5 g, 17.5 mmol), chlorotrimethylsilane (11.1 ml, 87.5 mmol) and sodium iodide (13.1 g, 87.5 mmol) in 10 ml of acetonitrile was heated at reflux for 12 hours. The mixture was then cooled to room temperature and diluted with ethyl acetate. The reaction mixture was washed repeatedly with 5 percent aqueous sodium bisulfite until the organic solution was colorless. Then it was washed with brine, dried over anhydrous magnesium sulfate, filtered and concentrated to provide 3.2 g (71 percent yield by weight) of adipic acid monosuccinimidyl ester as a white solid.

Proton NMR in CDCl₃ at 100 MHz (relative to TMS as internal standard): delta 3.90 (singlet, 4H), 2.70 (multiplet, 2H), 2.4 (multiplet, 2H), 1.80 (multiplet, 4H).

A mixture of adipic acid succinimidyl ester (1.00 g, 3.80 mmol) and thionyl chloride (5 ml) was heated at 40° degrees C. for three hours, then cooled to room temperature and concentrated in vacuo. The residue was stirred several times with dry hexane, the oil was separated and dried in vacuo to provide 0.97 g (90 percent yield by weight) of succinimidyl adipoyl chloride. This was dissolved in dry tetrahydrofuran to make a 5 molar solution, which was used as such in the preparation of compounds suitable for coupling to protein carriers.

Proton NMR in CDCl₃ at 100 MHz (relative to TMS as internal standard): 3.00 (multiplet, 2H), 2.90 (singlet, 4H), 2.70 (multiplet, 2H), 1.80 (multiplet 4H).

Succinimidyl glutaroyl chloride [5-[(2,5-dioxo-1-pyrolidinyl)oxy]-5-oxo-pentanoyl chloride] was similarly prepared and is utilized as discussed hereinafter.

VI. Preparation of Conjugates and Inocula

Conjugates of haptenic ligand molecules with protein carriers such as keyhole limpet hemocyanin (KLH) or bovine serum albumin (BSA) can be prepared, for example, by activation of the carrier with a coupling agent such as MBS (m-maleimidobenzoyl-N-hydroxy succinimide ester), and coupling to the thiol group of the haptenic ligand. See, for example, Liu et al., *Biochem.*, 80, 690 (1979). As is also well known in the art, it is often beneficial to bind a compound to its carrier by means of an intermediate, linking group.

Useful carriers are well known in the art and are generally proteins themselves. Exemplary of such carriers are keyhole limpet hemocyanin (KLH), edestin, thyroglobulin, albumins such as bovine serum albumin or human serum albumin (BSA or HSA, respectively), red blood cells such as sheep erythrocytes (SRBC), tetanus toxoid, cholera toxoid as well as polyamino acids such as poly(D-lysine:D-glutamic acid), and the like.

The choice of carrier is more dependent upon the ultimate intended use of the antigen than upon the determinant portion of the antigen, and is based upon criteria not particularly involved in the present invention. For example, if the conjugate is to be used in laboratory animals, a carrier that does not generate an untoward reaction in the particular animal should be selected.

The carrier-hapten conjugate is dissolved or dispersed in an aqueous composition of a physiologically tolerable diluent such as normal saline, PBS, or sterile water to form an inoculum. An adjuvant such as complete or incomplete Freund's adjuvant or alum can also be included in the inoculum. The inoculum is introduced as by injection into the animal used to raise the antibodies in an amount sufficient to induce antibodies, as is well known.

Exemplary immunogenic conjugates were prepared from a haptenic ligand by adapting their syntheses to incorporate a straight chain of carbon atoms on the haptenic ligand benzyl group (corresponding to the phenolic portion of the reactant ligand ester) as a spacing element, as noted before. Other exemplary immunogenic conjugates can be prepared as a spacing/linking element from a haptenic ligand by adapting these syntheses to incorporate the straight chain of carbon atoms on the portion of the haptenic ligand corresponding to the acid portion of the reactant ligand.

It was concluded that the flexible carbon chain of an adipate or glutarate appendage would reduce any bias to immunoreactivity due to the conformational constraint imposed by covalent attachment to the carrier protein. The bifunctional reagent prepared for this purpose also delivers the preactivated carboxyl group for linkage via amide bond formation with the lysine residues of the carrier. The particular coupling method used in this study is further described herein. The haptenic ligands were coupled to keyhole limpet hemocyanin (KLH) through an amino group of the phenolic portion of the structure.

According to the present invention, the intermediate linking agent is preferably succinimidyl adipoyl or glutaroyl chloride which was prepared as discussed before. An antigenic (immunogenic) conjugate is prepared as follows.

In an exemplary procedure, 2.5 mg of an above reaction product of hapten and succinimidyl adipoyl chloride or succinimidyl glutaroyl chloride in 250 $\mu$l of dimethylformamide is slowly added with stirring to 2 mg of KLH in 750 $\mu$l of 0.01 M sodium phosphate buffer at a pH value of 7.2. A temperature of 4° degrees C. is utilized and the resulting admixture is stirred for about one hour to form the hapten-linked KLH conjugate. The conjugate reaction product s formed is thereafter purified by usual means.

VII. Preparation of Monoclonal Receptors

The foregoing KLH conjugates (about 100 $\mu$g) were used to immunize groups of four 8-week old mice (129G1X+strain) by intraperitoneal (IP) injection in complete Freund's adjuvant. A further IP injection of 50 $\mu$g of a conjugate in alum was given two weeks thereafter. One month thereafter, the mouse with the highest antibody titer to the hapten was injected intravenously with 50 $\mu$g of the KLH-conjugate. The spleens were taken three days thereafter for preparation of hybridomas and monoclonal antibodies.

Monoclonal antibodies were obtained as described by Niman et al., *Proc. Natl. Acad. Sci. USA.* 77, 4524 (1980) and Niman et al., in *Monoclonal Antibodies and T-Cell Products*, ed., Katz, D. H., 23–51 (CRC Press, Boca Raton, Fl. 1982). Briefly, spleen cells $1 \times 10^8$) were fused with 2.0×10 Sp2/ myeloma cells. Cells were plated into 45 96-well plates; each well containing 150 $\mu$l of HAT-DMEM medium additionally containing 1 percent nutridoma and 2 percent BSA. The lymphocytes employed to form the hybridomas of the present invention may be derived from any mammal, such as a primate, rodent (e.g., mouse or rat), rabbit, guinea pig, cow, dog, sheep, pig or the like. As appropriate, the host may be sensitized by injection of the immunogen, in this instance a haptenic ligand, followed by a booster injection, and then isolation of the spleen.

It is preferred that the myeloma cell line be from the same species as the lymphocytes. Therefore, fused hybrids such as mouse-mouse hybrids [Shulman et al., *Nature* 276, 269 (1978)] or rat-rat hybrids [Galfre et al., *Nature.* 277, 131 (1979)] are typically utilized. However, some rat-mouse hybrids have also been successfully used in forming hybridomas [Goding, "Production of Monoclonal Antibodies by Cell Fusion," in *Antibody as a Tool*, Marchalonis et al. eds., John Wiley & Sons Ltd., p. 273 (1982)]. Suitable myeloma lines for use in the present invention include MPC-11 (ATCC CRL 167), p3×63-Ag8.653 (ATCC CRL 580), Sp2/O-Ag14 (ATCC CRL 1581), P3×63 Ag8U.1 (ATCC CRL 1597), Y3-Ag1.2.3. (deposited at Collection Nationale de Cultures de Microorganisms, Paris, France, number I-078) and P3×63Ag8 (ATCC TIB 9). The non-secreting murine myeloma line Sp2/O or Sp2O-Ag14 is preferred for use in the present invention.

The hybridoma cells that are ultimately produced can be cultured following usual in vitro tissue culture techniques for such cells as are well known. More preferably, the hybridoma cells are cultured in animals using similarly well known techniques with the monoclonal receptors being obtained from the ascites fluid so generated. The animals used for generation of the ascites fluid were Balb/c×129G1X+mice bred in the mouse colony of the Scripps Clinic and Research Foundation, La Jolla, Calif., however, when animals other than mice are used for preparation of the hybridomas, mice or that animal type can be used for the production of ascites fluid.

In particular, an exemplary monoclonal receptor was produced by the standard hybridoma technology of Kohler et al., *Nature*, 256, 495 (1975). Specifically, 129G1X mice were immunized by intraperitoneal injection with an inoculum of 100 micrograms of conjugate (e.g., Compound 1a, 2 or 5a bound to KLH) in 300 microliters of a 1:1 mixture of phosphate buffered saline (PBS) pH 7.4 and complete Freund's adjuvant. Two weeks later, the mice were again injected in a like manner with 50 micrograms of the foregoing conjugate in 300 microliters of a 1:1 mixture of PBS (pH 7.4) and 10 mg/ml alum. After an additional eight weeks, the mice were immunized intravenously with 50 micrograms of the conjugate in 200 microliters of PBS (pH 7.4). The spleens were removed from the mice 4 days later, and the spleen cells were fused to myeloma cells.

The spleens cells were pooled and a single cell suspension was made. Nucleated spleen cells ($1.4 \times 10^8$) were then fused with $3 \times 10^7$ Sp2/O non-secreting myeloma cells in the presence of a cell fusion promoter (polyethylene glycol 2000). The hybridoma that produces a particular monoclonal antibody was selected by seeding the hybridoma cells in 96-well plates and by growth in Dulbecco's modified Eagle medium (DMEM) containing 4500 mg/liter glucose (10 percent), 10 percent fetal calf serum (FCS), hypoxanthine, aminopterin and thymidine (i.e., HAT medium) which does not support growth of the unfused myeloma cells.

After two to three weeks, the supernatant above the cell clone in each well was sampled and tested by an ELISA assay (enzyme linked immunosorbent assay as described hereafter) for the presence of antibodies against Compound 1a, 2 or 5 as antigens. Each haptenic ligand was conjugated to BSA for the ELISA assays. Positive wells were cloned twice by limiting dilution. Those clones that continued to produce Compound 1a- or 2-specific antibody after two clonings were expanded to produce larger volumes of supernatant fluid.

Seven of the twenty-three monoclonal receptors (about 30 percent) that immunoreacted with Compound 1a catalytically hydrolyzed reactant ligand esters Compound 3. Each of those catalyses could be inhibited by an appropriate haptenic ligand such as Compound 1b. Thus, a relatively high percentage of induced monoclonal receptors was capable of catalyzing an esterolytic reaction. None of the twenty-one antibodies induced by hapten Compound 2 exhibited catalytic activity toward reactant ligand Compound 3. Similarly, colonies that initially produced antibodies that bound Compounds 5a, 6 or 7 were subcloned twice after which eighteen for Compound 5a, twenty-two for Compound 6 and twenty-six for Compound 7 remained active. These antibodies were of the IgG class.

Monoclonal catalytic molecules were precipitated from the ascitic fluids grown in pristane-primed Balb/c $\times$ 129G1X+mice with salt, purified by anion exchange chromatography (DEAE), followed by affinity chromatography (protein G), and dialyzed into 50 mM phosphate (100 mM NaCl, pH 7.5). Antibodies were judged to be homogeneous (95 percent) by sodium dodecyl sulfate polyacrylamide gel electrophoresis.

One of the hybridomas, denominated 30C6 was studied further and has been deposited at the American Type Culture Collection (ATCC), 12301 Parklawn Drive, Rockville, Md. This hybridoma was deposited on Jan. 24, 1990 and received accession number HB 10341. Two other hybridomas 27A6 and 57G11 were similarly deposited with the ATCC on December 11, 1990, and received accession numbers HB 10621 and HB 0622, respectively.

The present deposits were made in compliance with the Budapest Treaty requirements that the duration of the deposits should be for 30 years from the date of deposit or for 5 years after the last request for the deposit at the depository or for the enforceable life of a U.S. patent that matures from this application, whichever is longer. The hybridomas will be replenished should they become non-viable at the depository.

A monoclonal receptor of the present invention can also be produced by introducing, as by injection, the hybridoma into the peritoneal cavity of a mammal such as a mouse. Preferably, as already noted, syngeneic or semi-syngeneic mammals are used, as in U.S. Pat. No. 4,361,549, the disclosure of which is incorporated herein by reference. The introduction of the hybridoma causes formation of antibody-producing hybridomas after a suitable period of growth, e.g. 1-2 weeks, and results in a high concentration of the receptor being produced that can be recovered from the bloodstream and peritoneal exudate (ascites) of the host mouse. Although the host mice also have normal receptors in their blood and ascites, the concentration of normal receptors is typically only about five percent that of the monoclonal receptor concentration.

The monoclonal receptor present in the hybridoma supernatant can be used without purification or the receptor can be recovered from the ascites or serum of the mouse using standard techniques such as affinity chromatography using AD 169-infected cells bound to an immunosorbant such as Sepharose 6B or 4B (Pharmacia Fine Chemicals, Piscataway, N.J.), followed by elution from the immunosorbant using an acidic buffer such as glycine hydrochloride at a pH value of about 2.5.

In the present studies, IgG fractions were typically obtained from mouse ascites by precipitation with 45 percent saturated ammonium sulfate followed by chromatography on DEAE-Sephacel with sodium chloride elution as noted before. The fraction that was eluted with 100 mM salt was dialyzed and concentrated.

VIII. Enzyme-linked Immunosorbent Assay (ELISA)

The binding of ligands and the effect of chemical modification were assayed by ELISA with antibody at fixed concentration in the range of its titer and varying reagent or ligand concentration. Inhibition is reported if the titer is reduced 50 percent at less than a 1000:1 ratio of reagent to hapten.

Assays were performed in flat-bottom polyvinyl microtiter plates (Dynatech, Alexandria, Va.). Illustratively, the wells were coated with a solution comprising Compound 1a bound to BSA as the antigen ligand in phosphate buffered saline (PBS) using 50 microliters of solution per well. Ligands were coated at 1 microgram per milliliter. The plates were then incubated overnight at 37° degrees C. in a dry oven. The dried plates were stored at 4° degrees C. until use. Prior to the ELISA assay, dried plates were rehydrated by two washes of 2 minutes each with 10 millimolar (mM) PBS, pH 7.4, containing 0.1 percent polyoxalkylene (20) sorbitan monolaurate (Tween 20) and 0.02 percent Thimerosal (sodium ethylmercurithiosalicylate), (Sigma, St. Louis, Mo.).

In order to reduce non-specific binding, hybridoma supernatants were diluted 1:2 in washing buffer containing 0.1 percent BSA as diluent. Fifty microliters of diluted hybridoma supernatants were thereafter added to each well and incubated for 1 hour at 4° degrees C. on a gyroshaker to contact the monoclonal antibody-containing supernatant with the bound Compound 4. Following two washes of 2 minutes each, 50 microliters of peroxidase-labeled goat anti-mouse IgG+IgM (Tago, Burlingame, Calif.), diluted 1:1000, were added to each well, and the reaction mixture was incubated at 4° degrees C. for one hour to bind the labeled antibody to bound monoclonal antibody.

The substrate used to assay bound peroxidase activity was prepared just prior to use and consisted of 400 microgram/ml o-phenylenediamine (Sigma, St. Louis, Mo.) in 80 mM citrate-phosphate buffer, pH 6.0, containing 0.12 percent $H_2O_2$. After two final washes, 50 microliters of substrate solution were added to each well, and color was allowed to develop for 15 minutes in the dark. Color development was stopped by adding 25 microliters of 4 molar (M) $H_2SO_4$ to each well and the optical density at 492 nanometers (nm) was measured With a Multiskan ELISA plate reader.

IX. Kinetic Measurements

Purified monoclonal antibodies were dialyzed against EPPS buffer (I mM, pH 8.0, 100 mM NaCl) or CHES buffer (1 mM, pH 8.0, 100 mM NaCl). Its protein concentration was determined by the BCA method (Pierce). Assays were performed by HPLC (reverse-phase column, $C_{18}$, VYDAC 201Tp54) with $C_3CN/H_2O$ (0.1 percent TFA) on an isocratic program of 10/90. An internal standard of o-acetamidophenol was used to calculate the amount of product formed [4-(carboxybutyramido)phenol].

Antibody stock solutions were diluted into 1 ml of the appropriate buffer [50 mM, EPPS (pH 7.2-8.6); CHES (pH 8.6-10.0), 100 mM NaCl] to give a final protein concentration of 20 $\mu$M. Reactions contained 5 percent cosolvent dioxane, and the temperature was maintained at 37°±0.1°degrees C. Initial linear rates were measured at <5 percent hydrolysis of the total substrate. Antibodies tested were found to be stable for at least 48 hours under reaction conditions as determined by ELISA binding assays. The observed rates were corrected for the uncatalyzed rate of hydrolysis in the absence of antibody. Kinetic parameters $V_{max}$ $K_m$ were determined by nonlinear least-squares fitting of the initial rate vs. substrate concentration to a hyperbolic curve described by the Michaelis-Menten equation.

The variation of initial rates as a function of pH was measured in CHES (50 mM) (100 mM NaCl) at a pH value above 8.6 and in EPPS (50 mM) (100 mM NaCl) otherwise. There was no difference in the observed rates with antibody 27A6, when tested at pH 8.6 in EPPS and CHES (50 mM) (100 mM NaCl). Variation of the buffer ion concentration (12.5-50 mM) showed no dependency of $K_{cat}$, (antibody 27A6)[4] on the presence of the buffer species.

Equation 1 describes the pH rate profile obtained for the rate of hydrolysis ($K_{obed}$) of Compound 3 extrapolated to zero buffer concentration. Bruice et al. *Bioorganic Chemistry*, Vol. 1; Benjamin: New York (1965).

$$K_{obed} = K_{OH}[OH^+] \quad \text{Equation 1}$$

The line of solid squares (FIG. 3b) was generated by varying the concentration of buffer (12.5 mM-50 mM) at a fixed concentration of Compound 3 (400 $\mu$M) over the pH range 7.2-10.0. The buffers employed and their pH range tested were exactly the same as described above. The value of $K_{OH}$, may be calculated from the slope of a plot of $K_{obs}$ vs. $Kw/a_H$.

X. Chemical Modification of Antibodies (a) Phenylglyoxal; a 50 $\mu$l aliquot of a phenylglyoxal solution (6 mM), (125 mM NaHCO$_3$, pH 7.5) was added to buffer 195 $\mu$l (125 mM, pH 7.5 NaHCO$_3$), containing antibody (20 $\mu$M). The mixture was vortexed and left to stand for one hour at room temperature. This reaction mixture was then transferred to a microdialyzer (Pierce) and dialyzed with 125 mM, pH 7.5 NaHCO$_3$ with a flow through of approximately 150 ml/hour for two hours. The microdialyzer was then flushed with 4×60 ml portions of pH 8.4, 50 mM CHES, 100 mM NaCl and left to stand in this buffer overnight (about 15-18 hours). The microdialyzer was again flushed 3×50 ml portions of pH 8.4, 50 mM CHES, 100 mM NaCl the next morning. Samples were removed, protein concentrations recalculated (BCA) and assays run for catalytic activity (HPLC) or binding (ELISA). A similar procedure was used with hapten present (200 $\mu$M).

(b) Maleic anhydride; a 5 ml aliquot of a maleic anhydride solution (0.06 M, dioxane) was added to 299 $\mu$l of 20 mM, pH 8.9 borate, 100 mM NaCl containing 20 $\mu$M of antibody. The solution was vortexed and left to stand at room temperature for one hour. This reaction mixture was then transferred to a microdialyzer and dialyzed as described above with 50 mM CHES, pH 8.4, 100 mM NaCl. Samples were removed, protein concentrations calculated (BCA), and assays run for catalytic activity or binding.

(c) Diethyl pyrocarbonate; 10 $\mu$l of a 0.6 M diethylpyrocarbonate solution in ethanol was diluted into 1 ml of sodium acetate (NaOAc) (150 mM, pH 6, 100 mM NaCl). Five microliters of that solution were added to 299 $\mu$l of NaOAc (150 mM, pH 6.0, 100 mM NaCl) containing 20 M of antibody. The mixture was vortexed and left to stand at 4° degrees C. overnight (about 15-18 hours). This reaction mixture was then transferred to a microdialyzer and dialyzed as described above with CHES (50 mM, pH 8.4, 100 mM NaCl). Samples were removed, protein concentrations determined (BCA) and assays performed for catalytic activity and binding.

The foregoing is intended as illustrative of the present invention but not limiting. Numerous variations and modifications may be effected without departing from true spirit and scope of the invention.

What is claimed is:

1. Monoclonal antibody molecules or molecules containing antibody combining site portions that catalytically hydrolyze a preselected carboxylic acid ester bond of a reactant ligand, the antibody combining site of said molecules binding to:

(a) a reactant ligand containing the preselected carboxylic acid ester bond that is hydrolyzed; and (b) a haptenic ligand structurally analogous to said reactant ligand that contains a tetrahedral carbon atom bonded to a hydroxyl group as well as to a saturated carbon atom at a position in the haptenic ligand corresponding to the position of the carbonyl group as well as to the carbonyl-bonded heteroatom, respectively, of the preselected carboxylic acid ester bond to be hydrolyzed, said haptenic ligand further including a group that bears an ionic charge in aqueous solution at physiological pH values, the ionic charge-bearing group being absent from a corresponding position of said reactant ligand and located within a spherical volume defined by a radius of about 7 Ångstroms from said tetrahedral carbon atom.

2. The molecules of claim 1 wherein said ionic charge-bearing group is bonded indirectly to said tetrahedral carbon atom with at least one atom separating said tetrahedral carbon atom from the atom of said ionic charge-bearing group that bears the ionic charge.

3. The molecules of claim 1 wherein said haptenic ligand contains an ammonium ion or a carboxylate ion at physiological pH values as said ionic charge-bearing group.

4. Monoclonal antibody molecules or molecules containing antibody combining site portions that catalytically hydrolyze a preselected carboxylic acid ester bond of a reactant ligand, the antibody combining site of said molecules binding to:

(a) a reactant ligand containing the preselected carboxylic acid ester bond that is hydrolyzed, said reactant ligand being represented by the structure

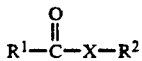

wherein
R$^1$ and R$^2$ represent carbon atom-containing chemical residues of the reactant, and
—X— is —O—; and (b) a haptenic ligand that is structurally analogous to said reactant ligand, said haptenic ligand being represented by the structure

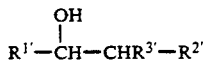

where R$^{1'}$ and R$^{2'}$ represent carbon atom-containing residues that are structurally analogous to R$^1$ and R$^2$, respectively, and at least one of R$^{1'}$ and R$^{2'}$ containing a group bearing an ionic charge in aqueous solution at physiological pH values, at least one said group providing ionic charge at physiological pH values being located within a spherical volume defined by a radius of about 7 Ångstroms from said

group of said structure, and R$^{3'}$ is H.

5. The molecules of claim 4 wherein said group bearing an ionic charge at physiological pH values is an ammonium ion or a carboxylate ion.

6. The molecules of claim 5 that are secreted by hybridoma 30C6 having ATCC accession number HB 10341.

7. The molecules of claim 5 that are secreted by hybridoma 27A6 having ATCC accession number HB 10621.

8. The molecules of claim 4 wherein said ionic charge-bearing group is bonded indirectly to the tetrahedral carbon atom of said

group with at least one atom separating said tetrahedral carbon atom from the atom of said charge-bearing group that bears the ionic charge, and wherein said ionic charge-bearing group is located within a spherical volume defined by a radius of about 2 to about 5 Ångstroms from said tetrahedral carbon atom.

9. Cells that when cultured in a medium produce monoclonal antibody molecules or molecules containing antibody combining site portions that catalytically hydrolyze a preselected carboxylic acid ester bond of a reactant ligand, the antibody combining site of said molecules binding to:

(a) a reactant ligand containing the preselected carboxylic acid ester bond that is hydrolyzed; and (b) a haptenic ligand structurally analogous to said reactant ligand that contains a tetrahedral carbon atom bonded to a hydroxyl group as well as to a saturated carbon atom at a position in the haptenic ligand corresponding to the position of the carbonyl group as well as to the carbonyl-bonded heteroatom, respectively, of the preselected carboxylic acid ester bond to be hydrolyzed, said haptenic ligand further including a group bearing an ionic charge in aqueous solution at physiological pH values, the ionic charge-bearing group being absent from said reactant ligand and located within a spherical volume defined by a radius of about 7 Ångstroms from said tetrahedral carbon atom.

10. The cells of claim 9 that are hybridoma cells that further secrete into the culture medium said monoclonal antibody molecules or molecules containing antibody combining site portions that catalytically hydrolyze said preselected carboxylic acid ester bond.

11. The hybridoma cells of claim 10 that are those of hybridoma 30C6 having ATCC accession number HB 10341.

12. The hybridoma cells of claim 10 that are those of hybridoma 27A6 having ATCC accession number HB 10621.

13. A method of catalytically hydrolyzing a preselected ester bond in a reactive ligand molecule comprising the steps of:

(a) admixing a catalytically effective amount of the monoclonal antibody molecules or molecules containing antibody combining site portions of claim 1 with said reactant ligand molecules in an aqueous medium to form a reaction admixture; and (b) maintaining said reaction admixture for a period of time sufficient for said reactant ligand molecules to bind to said antibody molecules or molecules containing antibody combining site portions and for said antibody molecules or molecules containing antibody combining site portions thereof to catalytically hydrolyze said preselected bond and form products.

14. The method of claim 13 wherein said antibody molecules or molecules containing antibody combining site portions thereof are secreted by hybridoma 30C6 having ATCC accession number HB 10341 or hybridoma 27A6 having ATCC accession number HB 10621.

15. A method of preparing cells that when cultured in a medium produce antibody molecules or molecules containing antibody combining site portions that catalytically hydrolyze a preselected carboxylic acid ester bond of a reactant ligand comprising the steps of:

(a) immunizing an animal with an immunogen that includes a haptenic ligand that contains a tetrahedral carbon atom bonded to a hydroxyl group as well as to a saturated carbon atom at a position in the haptenic ligand corresponding to the position of the carbonyl group as well as to the carbonyl-bonded heteroatom, respectively, of the preselected carboxylic acid ester bond to be hydrolyzed, said haptenic ligand further including a group bearing an ionic charge in aqueous solution at physiological pH values, the ionic charge-bearing group being absent from a corresponding position of said reactant ligand and located within a spherical volume defined by a radius of about 7 Ångstroms from said tetrahedral carbon atom;

(b) maintaining said animal for a time period sufficient for said animal to secrete antibodies that immunoreact with said haptenic ligand;

(c) transferring genes that encode antibody molecules or molecules containing antibody combining site portions from antibody-producing cells of said maintained, immunized animal of step (b) into host cells to form hybrid cells that contain genes from at least two sources, and which formed hybrid cells (i) produce antibody molecules or molecules containing antibody combining site portions from said transferred genes when cultured and (ii) can be cultured substantially indefinitely;

(d) culturing the hybrid cells in an appropriate culture medium for a time period sufficient for those hybrid cells to produce antibody molecules or molecules containing antibody combining site portions;

(e) recovering antibody molecules or molecules containing antibody combining site portions from the cultured hybrid cells;

(f) screening the obtained antibody molecules or molecules containing antibody combining site portions to identify a hybrid cell that produces antibody molecules or molecules containing antibody combining site portions that catalytically hydrolyze said predetermined carboxylic acid ester bond; and (g) growing clones of said identified hybrid cell that produces antibody molecules or molecules containing antibody combining site portions that catalytically hydrolyze said predetermined carboxylic acid ester bond.

16. The method of claim 15 wherein the cells formed in step (c) are hybridoma cells.

* * * * *

UNITED STATES PATENT AND TRADEMARK OFFICE
CERTIFICATE OF CORRECTION

PATENT NO.    : 5,187,086
DATED         : February 16, 1993
INVENTOR(S)   : Kim Janda It is certified that error appears in the above-identified patent and that said Letters Patent is hereby corrected as shown below:

Column 1,
Line 10, before the heading "Cross-Reference to Related Application", replace the governmental support paragraph with the following paragraph:

-- This invention was made with government support under Contract No. GM 43858 by the National Institutes of Health. The government has certain rights in this invention. --

Signed and Sealed this

Fifteenth Day of July, 2003

JAMES E. ROGAN
*Director of the United States Patent and Trademark Office*